US011364036B2

(12) United States Patent
Hassler, Jr. et al.

(10) Patent No.: US 11,364,036 B2
(45) Date of Patent: Jun. 21, 2022

(54) SAW FOR BLADE HAVING DEFORMABLE LOCK TEETH

(71) Applicant: Stryker European Operations Holdings LLC, Kalamazoo, MI (US)

(72) Inventors: William L. Hassler, Jr., Portage, MI (US); Graham L. Weeks, Holland, MI (US); Fintan Tynan, Kilkenny (IE); Sinead K. Hughes, County Meath (IE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 0 days.

(21) Appl. No.: 16/874,740

(22) Filed: May 15, 2020

(65) Prior Publication Data
US 2020/0275937 A1     Sep. 3, 2020

Related U.S. Application Data

(60) Division of application No. 15/679,554, filed on Aug. 17, 2017, now Pat. No. 10,667,826, which is a
(Continued)

(51) Int. Cl.
*A61B 17/14*      (2006.01)
*B23D 51/10*      (2006.01)
(Continued)

(52) U.S. Cl.
CPC ............ *A61B 17/142* (2016.11); *A61B 17/15* (2013.01); *B23D 51/10* (2013.01); *B23D 61/123* (2013.01);
(Continued)

(58) Field of Classification Search
CPC .. A61B 17/14–147; A61B 2017/00946; B23D 61/123; B23D 51/10; B27B 19/006
(Continued)

(56) References Cited

U.S. PATENT DOCUMENTS 3,943,934 A   3/1976 Bent
3,975,891 A   8/1976 Gunther
(Continued)

FOREIGN PATENT DOCUMENTS

DE   102012201624 A1   8/2013
EP       1090705 A2    4/2001
(Continued)

OTHER PUBLICATIONS

EPO, "ISA Written Opinion for PCT/US2016/018289", dated Mar. 2017.

*Primary Examiner* — Jason Daniel Prone
(74) *Attorney, Agent, or Firm* — Howard & Howard Attorneys PLLC

(57) ABSTRACT

A surgical saw includes a body, a coupling assembly, and a motor. The coupling assembly is mounted to the body and adapted to releasably hold a saw blade. The coupling assembly includes an anvil, a press, and a clamping assembly. The anvil has a channel or a press foot. The press has the other of the press foot and the channel. The press foot is receivable by the channel. The clamping assembly selectively moves the press and the anvil towards and away from each other. When the press is brought towards the anvil, the press foot may press a lock tooth of the saw blade into the channel so that the lock tooth is compressed between the anvil and the press to coin the lock tooth. The motor, internal to the body, is connected to the coupling assembly to reciprocate the coupling assembly and the saw blade.

15 Claims, 11 Drawing Sheets

Related U.S. Application Data continuation of application No. PCT/US2016/018289, filed on Feb. 17, 2016.

(60) Provisional application No. 62/118,336, filed on Feb. 19, 2015.

(51) Int. Cl.
- *B23D 61/12* (2006.01)
- *B27B 19/00* (2006.01)
- *A61B 17/15* (2006.01)
- *A61B 17/00* (2006.01)

(52) U.S. Cl.
CPC .. *B27B 19/006* (2013.01); *A61B 2017/00946* (2013.01)

(58) Field of Classification Search
USPC ...... 30/329, 337, 339, 392–394; 606/79, 82, 606/176–179; D8/20, 70; D24/146
See application file for complete search history.

(56) References Cited

U.S. PATENT DOCUMENTS

| | | | |
|---|---|---|---|
| 4,106,181 A | 8/1978 | Mattchen | |
| 4,140,524 A | 2/1979 | Oberholtzer et al. | |
| 4,386,609 A | 6/1983 | Mongeon | |
| 5,210,925 A | 5/1993 | Morgulis | |
| D343,247 S | 1/1994 | Walen | |
| D351,907 S | 10/1994 | Matthai et al. | |
| D360,946 S | 8/1995 | Goris | |
| 5,489,285 A | 2/1996 | Goris | |
| 5,496,316 A | 3/1996 | Goris | |
| 5,554,165 A | 9/1996 | Raitt et al. | |
| 5,674,184 A * | 10/1997 | Hassler, Jr. ........ | A61B 17/3417 600/175 |
| 5,702,415 A | 12/1997 | Matthai et al. | |
| 5,729,904 A | 3/1998 | Trott | |
| D394,315 S | 5/1998 | Fisher | |
| D406,223 S | 3/1999 | Tran | |
| 6,113,618 A | 9/2000 | Nic | |
| D459,805 S | 7/2002 | Pascaloff | |
| D489,823 S | 5/2004 | Fisher et al. | |
| 6,865,813 B2 | 3/2005 | Pollak | |
| 7,189,239 B2 | 3/2007 | Fisher et al. | |
| 7,704,254 B2 | 4/2010 | Walen | |
| 8,100,912 B2 | 1/2012 | Marietta | |
| 8,216,262 B2 | 7/2012 | O'Donoghue | |
| 8,316,550 B2 | 11/2012 | Howells | |
| 8,322,253 B2 | 12/2012 | Howells | |
| D694,599 S | 12/2013 | Davidian et al. | |
| 8,734,450 B2 | 5/2014 | Landon | |
| 8,852,221 B2 * | 10/2014 | Boykin ................ | A61B 17/142 606/171 |
| 8,920,424 B2 * | 12/2014 | Boykin ................ | A61B 17/142 606/82 |
| 8,936,597 B2 | 1/2015 | Wang et al. | |
| D741,135 S | 10/2015 | Yang et al. | |
| D741,136 S | 10/2015 | Yang et al. | |
| 9,242,361 B2 | 1/2016 | Kaye, Jr. et al. | |
| 9,414,845 B2 * | 8/2016 | Boykin ................ | A61B 17/142 |
| 9,517,074 B2 * | 12/2016 | Boykin ................ | A61B 17/142 |
| 9,522,007 B2 | 12/2016 | Servidio | |
| 9,566,074 B2 | 2/2017 | Milburn et al. | |
| 9,815,187 B2 | 11/2017 | Kozak | |
| D817,128 S | 5/2018 | Gopi | |
| 10,040,186 B2 | 8/2018 | Kaye, Jr. et al. | |
| 10,076,340 B2 * | 9/2018 | Belagali ................ | A61B 17/14 |
| 10,182,826 B2 | 1/2019 | Boykin et al. | |
| 10,239,135 B2 | 3/2019 | Desoutter et al. | |
| 10,245,716 B2 | 4/2019 | Kaye, Jr. et al. | |
| 10,265,778 B2 | 4/2019 | Kaye, Jr. et al. | |
| 10,667,826 B2 * | 6/2020 | Hassler, Jr. .......... | A61B 17/142 |
| 10,856,885 B2 * | 12/2020 | Boykin ................ | A61B 17/142 |
| 2004/0098000 A1 | 5/2004 | Kleinwaechter | |
| 2005/0192585 A1 | 9/2005 | Simmons | |
| 2009/0217537 A1 | 9/2009 | Macdonald et al. | |
| 2009/0312762 A1 | 12/2009 | Boykin | |
| 2009/0326540 A1 | 12/2009 | Estes | |
| 2010/0175532 A1 | 7/2010 | Evatt et al. | |
| 2011/0316241 A1 | 12/2011 | Zhang et al. | |
| 2011/0319719 A1 | 12/2011 | O'Prey et al. | |
| 2013/0205600 A1 | 8/2013 | Kehoe | |
| 2014/0018811 A1 | 1/2014 | Mootien et al. | |
| 2016/0257010 A1 | 9/2016 | Jones | |
| 2017/0182570 A1 | 6/2017 | Dvorak et al. | |
| 2017/0291238 A1 | 10/2017 | Bernardi et al. | |
| 2017/0340338 A1 | 11/2017 | Hassler, Jr. et al. | |
| 2017/0348007 A1 | 12/2017 | Shiels | |

FOREIGN PATENT DOCUMENTS

| | | | |
|---|---|---|---|
| EP | 1607058 A1 | 12/2005 | |
| EP | 1882538 A2 | 1/2008 | |
| EP | 2422725 A2 | 2/2012 | |
| EP | 3258859 B1 * | 6/2019 | ........... A61B 17/142 |
| EP | 3572013 A1 * | 11/2019 | ........... B27B 19/006 |
| WO | 8702311 A1 | 4/1987 | |
| WO | 2016134030 A2 | 8/2016 | |
| WO | WO-2016134030 A3 * | 4/2017 | ........... A61B 17/142 |

* cited by examiner

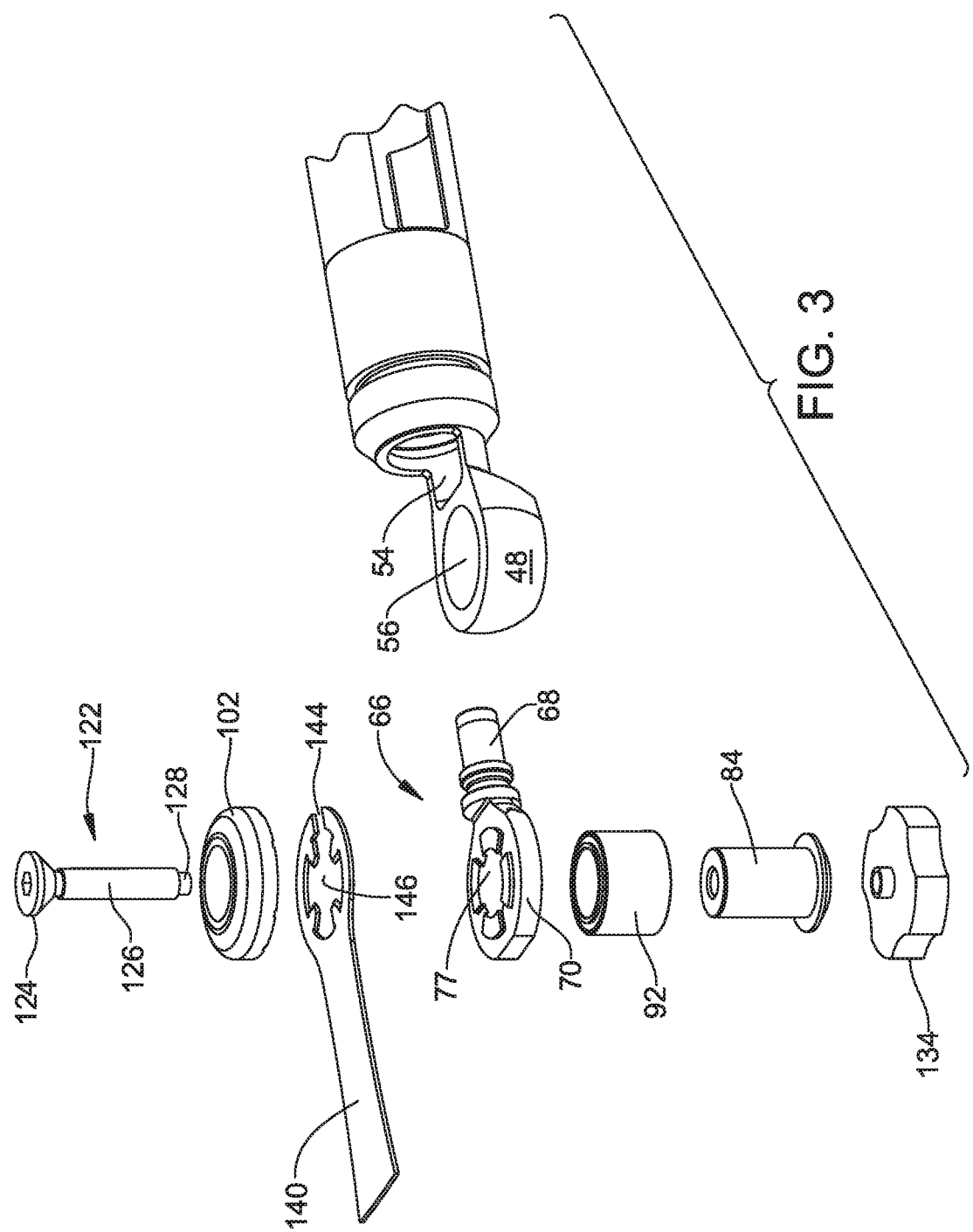

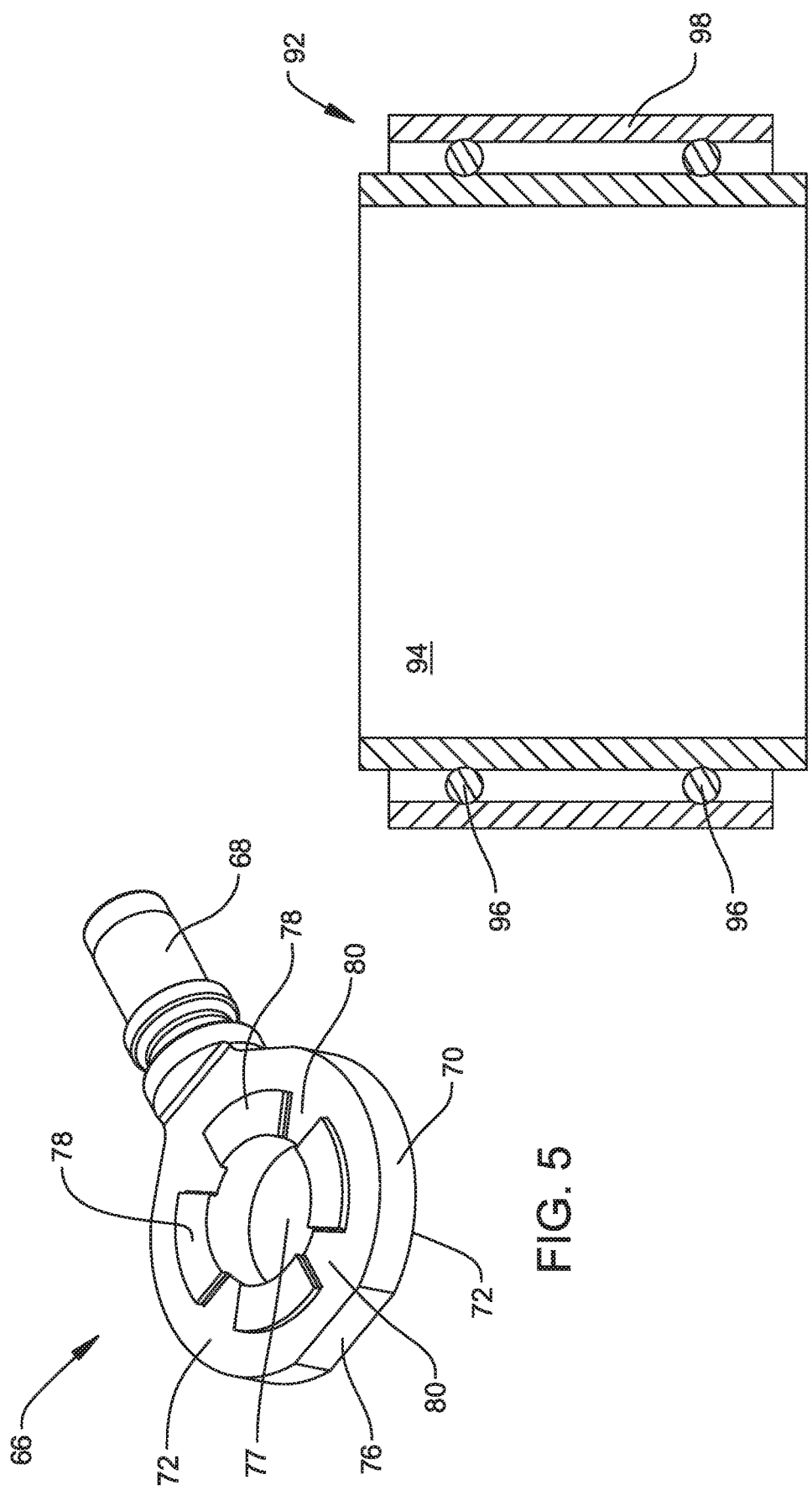

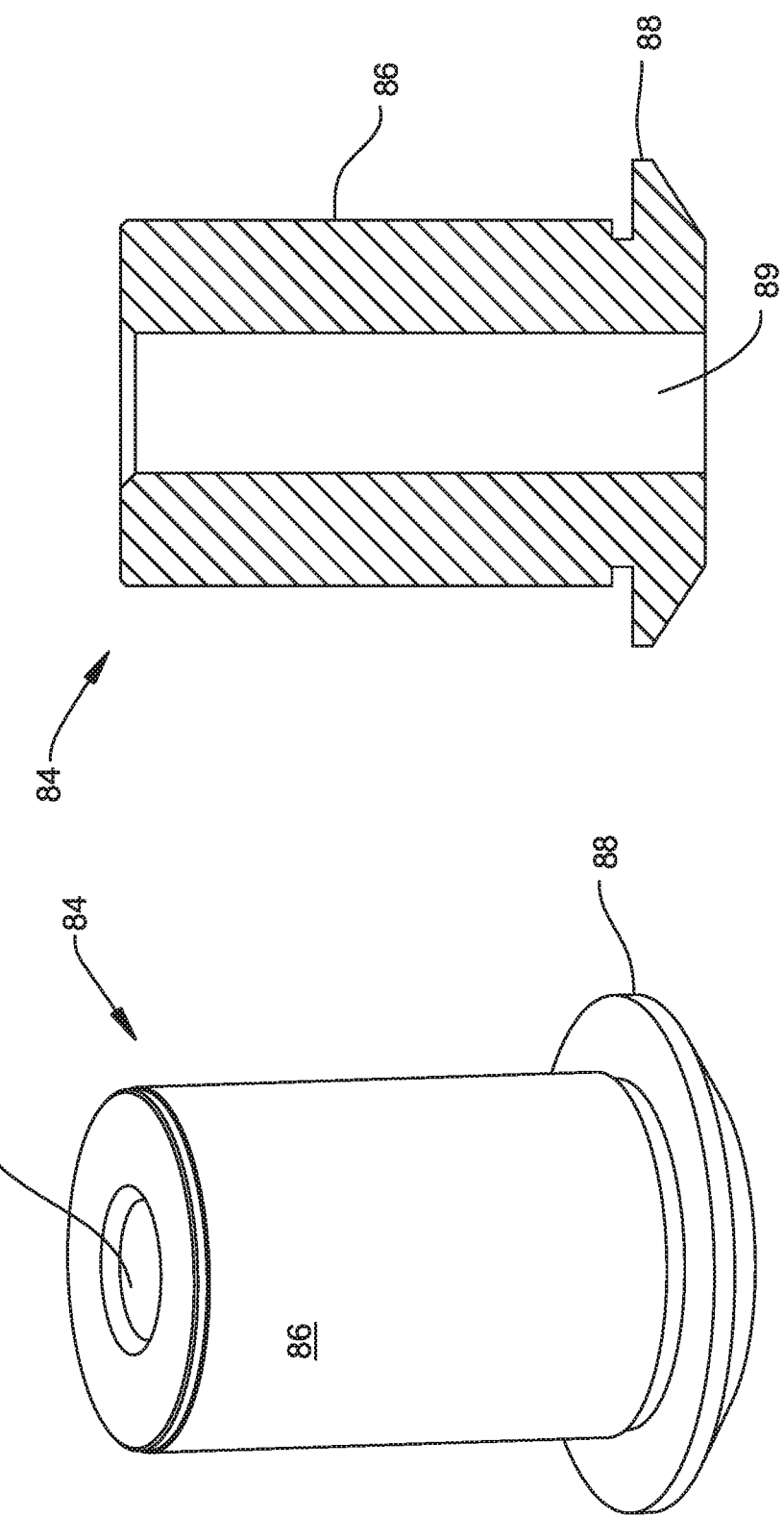

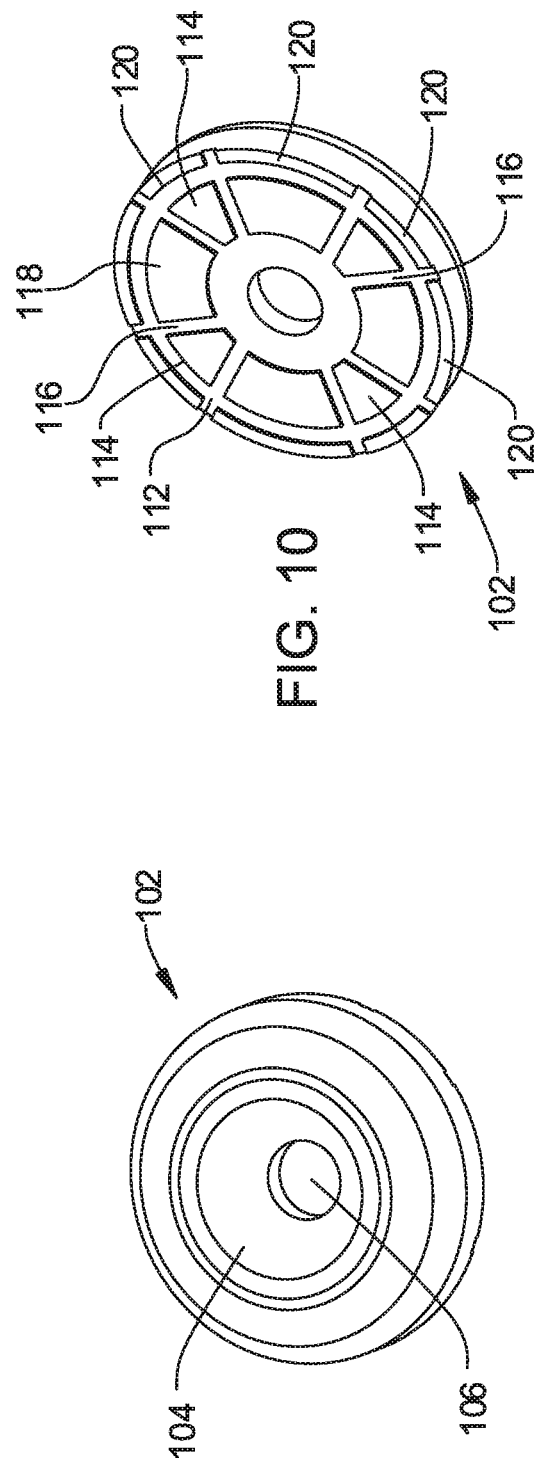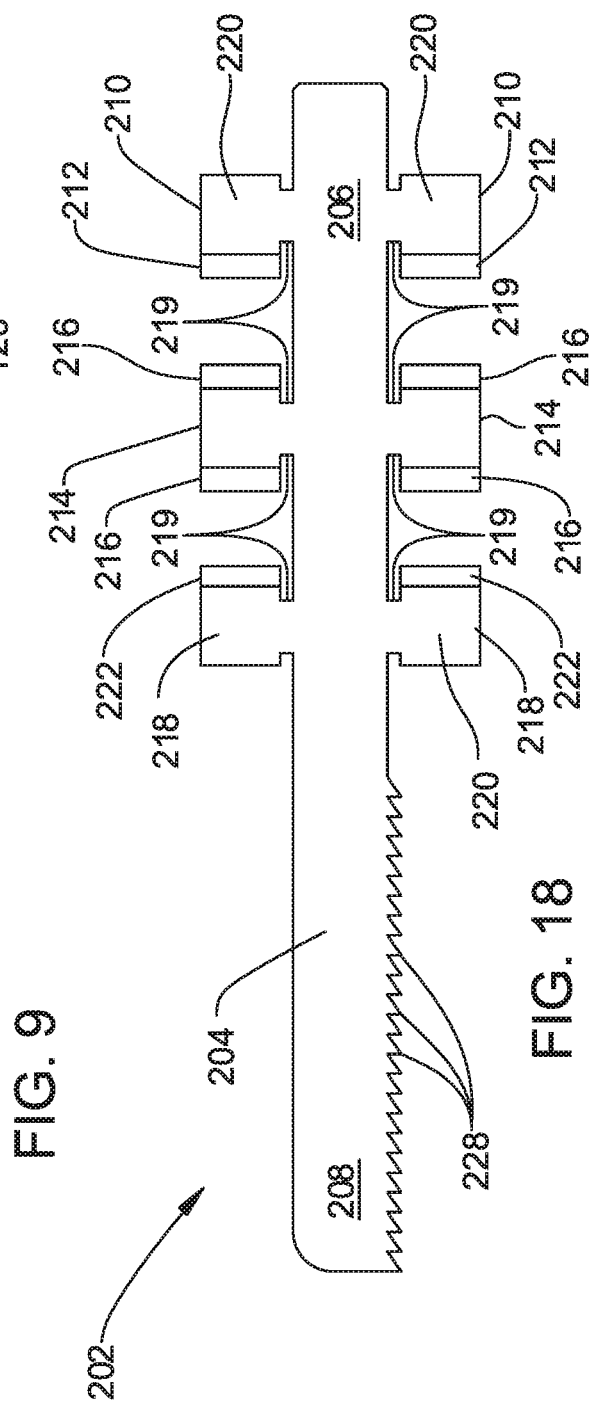

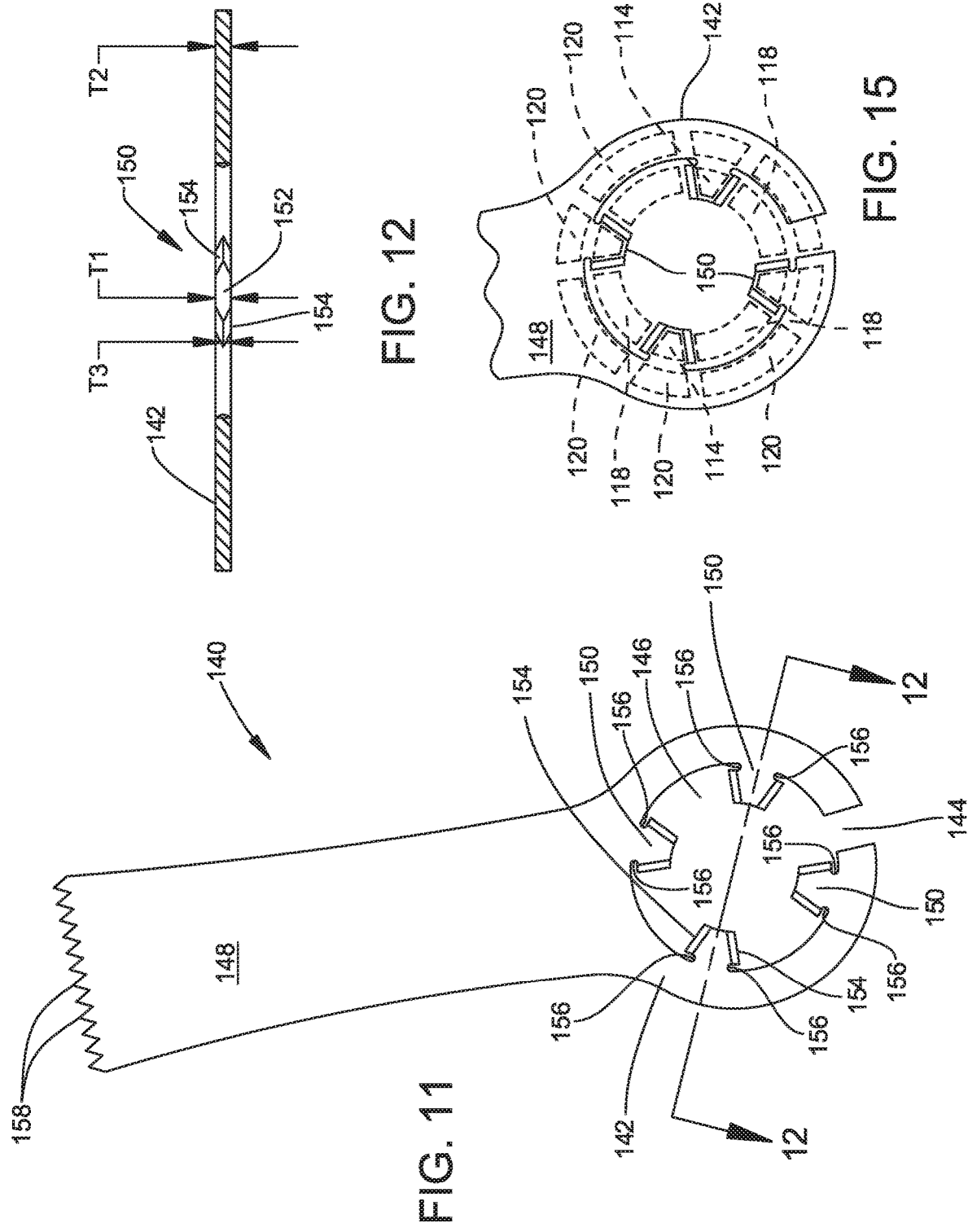

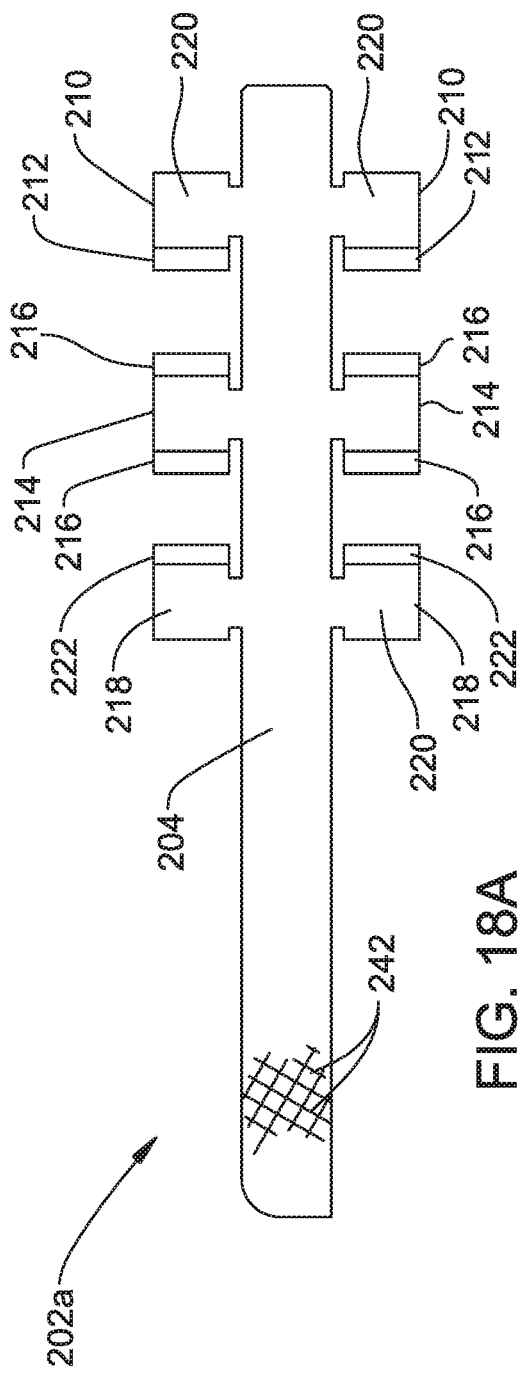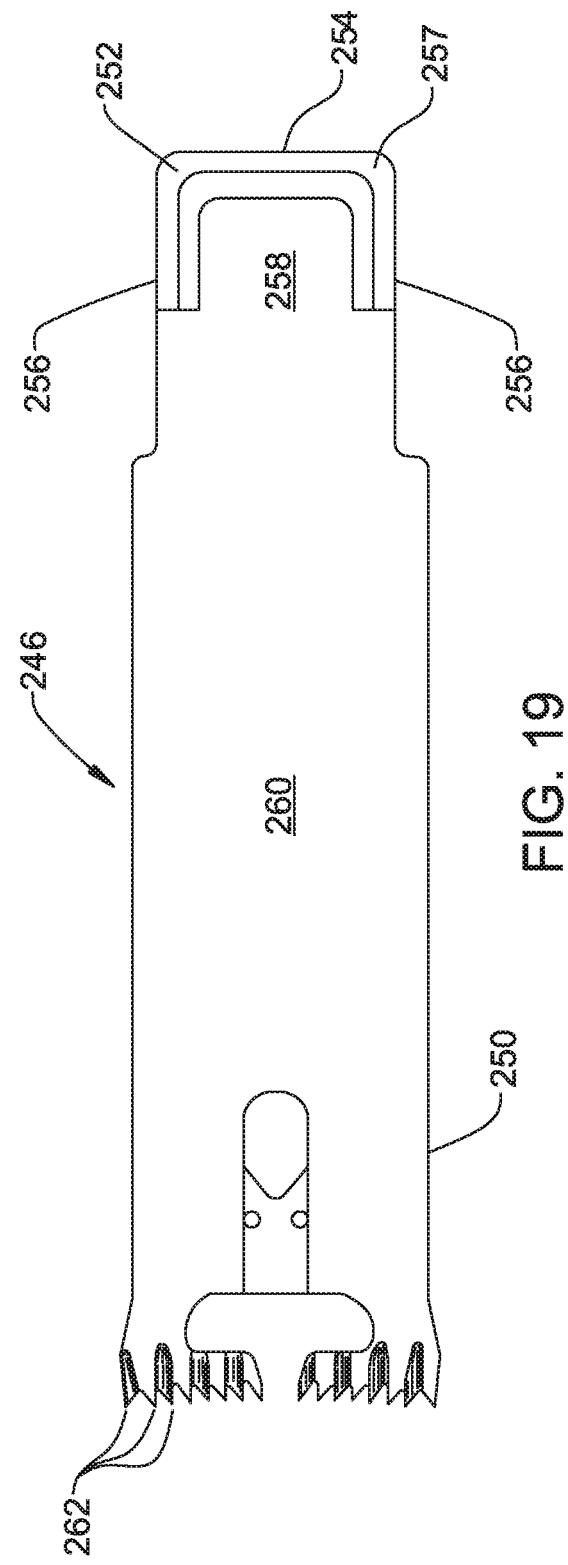

SAW FOR BLADE HAVING DEFORMABLE LOCK TEETH

RELATED APPLICATIONS

This application is a divisional of U.S. patent application Ser. No. 15/679,554 (now U.S. Pat. No. 10,667,826), filed Aug. 17, 2017, which is a continuation of PCT/US2016/018289, filed Feb. 17, 2016, which claims priority to and all the benefits of U.S. Provisional Patent Application Ser. No. 62/118,336 which was filed on Feb. 19, 2015, the entire contents of which are hereby incorporated by reference.

FIELD OF THE INVENTION

This invention generally relates to surgical saws and the complementary blades used with the saws. The invention relates to a saw and a blade with complementary features that deform the blade when the blade is mounted to the saw.

BACKGROUND OF THE INVENTION

A powered surgical instrument, a surgical tool, used with some frequency is the powered surgical saw. This type of instrument is used to remove tissue, including bone and cartilage. Attached to the saw is a saw blade. A drive assembly internal to the saw reciprocates the blade in a back and forth motion. Often the saw includes a moving head. The head is the component of the saw to which the blade is mounted. Some blades are constructed to pivot back and forth, oscillate, in the plane in which the blade is oriented. This type of blade is referred to as a sagittal saw blade. A sagittal saw blade is provided with teeth that extend forward from the distal end of the blade body.

Many sagittal saws and their complementary blades are designed so that the blade extends distally forward of the blade head. One such assembly is disclosed in the Applicant's U.S. Pat. No. 8,100,912/PCT Pub. No. WO 2007/011542, the contents of which are incorporated herein by reference. This type of saw and blade are used to remove a section of bone. This is perhaps the most common type of sagittal saw.

A surgical saw includes an assembly for removably holding the blade to the saw. This is because the blade is often the single use component of the combined saw and blade assembly. One reason the blade is used once is that upon use of the blade, the teeth are immediately dulled. Owing to the economics, it is often more cost effective to use a new blade with each patient than go to the expense of sterilizing and resharpening a previously used blade.

A surgical sagittal saw is typically formed so that the head has a slot. The slot is the void space dimensioned to receive the proximal end of the blade. Often, the proximal end of the blade is provided with one or more openings. Each opening is dimensioned to receive a pin that is moveably mounted to the saw head. The seating of the pin in the blade opening releasably holds the blade to the head.

It is common practice to collectively dimension the saw head and blade so the slot facilitates the close slip fitting of the blade in the slot. This dimensioning facilitates the relatively easy insertion of the blade into the saw head and removal of the blade from the saw head. A result of this component dimensioning is that within the slot, there is small clearance between the blade and the interior surfaces of the saw head that define the slot. This means that within the slot the blade has space to move.

Owing to this tendency of the blade to move, the back-and-forth movement of the blade is not always in phase with the back-and-forth movement of the saw head. This out of phase movement occurs because when the saw head reverses direction, owing to the blade having a momentum in the opposite direction, the blade continues to move in the first direction. Thus, there may be times in the movement of the saw head and blade where these two components move in the opposed directions. This can result in the blade striking an adjacent surface of the saw head. This action is sometimes referred to as blade slap. A result of blades continually slapping against the saw head is that the material forming the head can fatigue. This component fatigue can result in the fracturing of the saw head. Once such a fracture occurs, at a minimum, it is necessary to replace the saw head.

The failure of the blade to move completely in unison with the saw head can even result in problems even when the blade does not strike the saw head. The lagging movement of the blade relative to the saw head is sometimes referred to as backlash. As a result of this movement each tooth of the blade may not, in a single phase of a single oscillatory cycle, move in an arc of sufficient length. More particularly, for a blade to efficiently function, during a single phase of movement, a tooth of the blade should move at least as far as the starting position of the adjacent tooth at the start of the phase. For example, when a blade sweeps right, a tooth should move to the right a sufficient distance so that, at the end of the sweep, the tooth will have moved to at least the location at which the adjacent tooth to the right of the blade was located at the start of the sweep. When a tooth engages in this degree of arcuate movement, there is high likelihood that, in the single sweep the tooth will have sheared away the bone located between that tooth and the adjacent right located tooth. This removal of all the bone between the teeth is what facilitates the efficient formation of the cut.

The problem arises because, owing to the backlash, the saw blade and by extension the teeth of the saw, in a single phase of movement, engages in an arcuate movement that is less than the arcuate movement of the saw head. In some situations that means that in the single phase of movement, a blade will not sweep to the location at which the adjacent tooth was located at the start of the sweep. When this event occurs, not all the bone between the teeth are sheared, cut away. This can reduce the efficiency of the cutting process.

In addition to the blade moving side to side relative to the saw head, a blade may be able to move up and down relative the head slot in which the blade is seated. This movement is sometimes referred to as the out of plane oscillation of the blade. Alternatively, this movement is sometimes referred to as blade whip. This out of plane movement of the blade relative to the saw can adversely affect the precision of the cut formed by the blade. This movement can also stress both the saw head and the proximal end of the blade, the portion of the blade seated in the saw head slot. The stressing of the saw head can result in the fracturing of the saw head. The stressing of the proximal end of the blade can result in the deformation of the blade. This deformation can also reduce the precision of the cut made by the blade.

Another disadvantage of this movement of the blade relative to the saw head is that it can result in the blade moving to a less than optimal position for the procedure being performed. When a sagittal saw is used to remove a large section of the bone such as a portion of the knee, the blade is often placed in a resection guide. This instrument is a block that is affixed to the bone adjacent where the cut is to be formed. The block is formed with one or more slots. The slots serve as guide paths through which the saw blade is inserted. By cutting the bone along the guide paths defined by the slots, the bone left after the cut will have the desired shape. This precision shaping of the bone ensures the proper fitting of an orthopedic implant to the bone. Owing to the flexure of the blade when fitted in one of these slots, the blade can gall, wear the material that defines the slots. This can result in the shape of the slot deforming from the shape needed to ensure that a cut formed based on the shape of the slot has the desired shape. Once this deformation of the resection guide occurs, the guide is no longer useful.

There is therefore a desire to provide a surgical sagittal saw and complementary blade that are constructed so that, when the saw and blade are actuated, the saw head and blade move as a single rigid structure. One means to ensure the saw head and blade move as a single rigid body is to provide a clamping assembly that, when set, applies an appreciable amount of force to the blade to hold the blade to the saw head. This typically means that the individual charged with blade insertion and blade removal needs to apply a significant amount of force in order to reset and release the clamping assembly. Requiring the individual responsible to perform these tasks to apply these forces can complicate the process of inserting and removing the blade. Requiring the individual to apply these forces can also slow the processes associated with both inserting and removing the blade. This is especially true if the individual has limited arm and hand strength. Further, if these forces are not properly applied, especially the force required to set the clamping assembly, the blade may not be fully locked to the saw head. When the saw is actuated this could result in a clearly undesirable event, the blade working free from the saw.

SUMMARY OF THE INVENTION

This invention is related to a new and useful surgical saw and complementary blade for use with the saw. The saw and complementary blade of this invention are designed to ensure that, when the blade is removably attached to the head integral with the saw, the blade and saw head move as a single unit.

The blade of this invention is provided with one or more lock teeth. The lock teeth are formed from material that, in comparison to the material from which the blade body and cutting teeth are formed, is relatively soft.

The saw of this invention includes a head. The head includes an anvil and a press. The press is located adjacent the exposed surface of the anvil and is moveable towards and away from the anvil. At least one of the anvil or the press is formed to define one or more slots. Each slot is dimensioned to receive a separate one of the blade lock teeth. The press or the anvil is formed with press surfaces. The press surfaces are in registration with the slots formed in the other of the anvil or the press.

To removably mount a blade to the saw according to this invention, the press is first moved away from the anvil. The blade is placed between the anvil and the press so the one or more lock teeth seat in the complementary slots formed in the anvil or the press. The press is moved against the blade. More specifically, the press is displaced so that blade is compressed between the anvil and the press. As a result of this compression of the blade, the press surfaces push the lock teeth into the slots formed in the anvil or the press.

As a result of the lock teeth being pushed into the adjacent slots and the lock teeth being relatively soft, ductile, the lock teeth are deformed. Each lock tooth is deformed, becomes coined, around the surfaces of the anvil and the press that define the slots and the press surfaces. As a result of this deformation of the blade lock teeth, there is essentially no clearance between the lock teeth and the anvil and the press. The saw head and blade essentially become a single piece component. There is essentially no movement of the blade relative to the saw head.

In some versions of the invention, the blade lock teeth are further formed to have opposed faces. At least one tapered surface extends between the opposed faces. The tapered surfaces are the surfaces of the lock teeth that are disposed against the corners, the edges, of the saw head that define the slots and press surfaces. The portions of the lock teeth that define the tapered surfaces, during the process of locking the blade to the saw head, are the portions of the lock teeth that are coined.

In some versions of the invention, the press is a cap that is disposed over the anvil.

In some versions of the invention, the blade has plural sections. The sections of the blade that defines the one or more lock teeth are relatively soft. The remaining section of the blade, the section that defines the cutting teeth, is relatively hard. In some processes used to make this version of the invention, the stock from which the blade is formed is manufactured out of relatively hard material. The blade is selectively treated so as to result in the lock teeth being softer, more ductile, than the rest of the blade. In some processes used to make this version of the invention, the stock from which the blade is formed is relatively soft. More specifically, the stock is sufficiently ductile so that when pressure is applied to the lock teeth, the lock teeth will deform.

In some versions of the invention wherein the blade is formed out of materials of different hardnesses, the section of the blade defining the lock teeth is formed from a first material that is relatively soft. The majority, if not all of the rest of the blade is made out a material of sufficient hardness that it can cut the bone the blade is intended to cut.

In some versions of the invention, the proximal end of the blade is provided with a circularly shaped void. In some versions of this invention, at least one lock tooth extends inwardly from the perimeter of this void. In many versions of the invention, plural lock teeth extend inwardly into this void.

The saw and blade of this application may be designed as sagittal saws, oscillating saws or reciprocating saws. Also, for the purposes of this invention, a rasp is considered a type of saw blade.

BRIEF DESCRIPTION OF THE DRAWINGS

The invention is pointed out with particularity in the claims. The above and further features and advantages of this invention are understood from the following Detailed Description taken in conjunction with the accompanying drawings in which:

FIG. 3 is an exploded view of the saw assembly;

FIG. 5 is a perspective view of the drive link;

FIG. 6 is a perspective view of the pivot sleeve;

FIG. 7 is a cross sectional view of the pivot sleeve;

FIG. 8 is a cross sectional view of the bearing assembly to which the pivot sleeve is mounted;

FIG. 9 is a perspective view of the top of the cap;

FIG. 10 is a perspective view of the bottom of the cap;

FIG. 11 is a plan view of the blade of this invention;

FIG. 12 is a cross sectional view of the blade taken along line 12-12 of FIG. 11;

FIG. 15 is a plan view depicting the positions of the cap feet against the blade when the saw unit is in the run state;

FIG. 18 is a plan view of an alternative blade, specifically a reciprocating blade, constructed in accordance with this invention;

FIG. 18A is a plan version of an alternative construction of the version of the blade of FIG. 18, wherein the blade is constructed to function as a rasp;

FIG. 19 is a plan view of a second alternative blade of this invention; and

DETAILED DESCRIPTION

Figure 1:
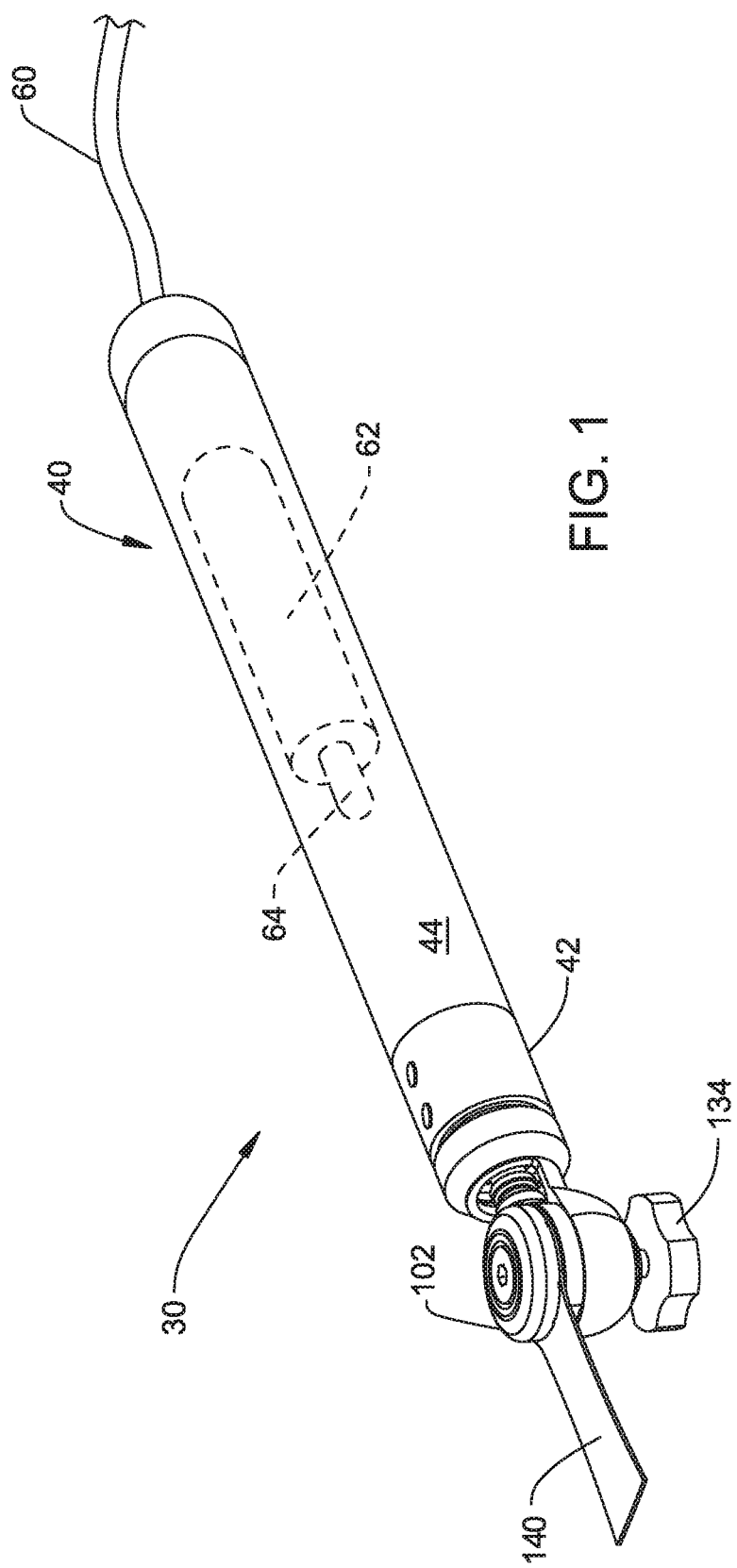
FIG. 1 is a perspective view of a saw assembly of this invention.
Figure 2:
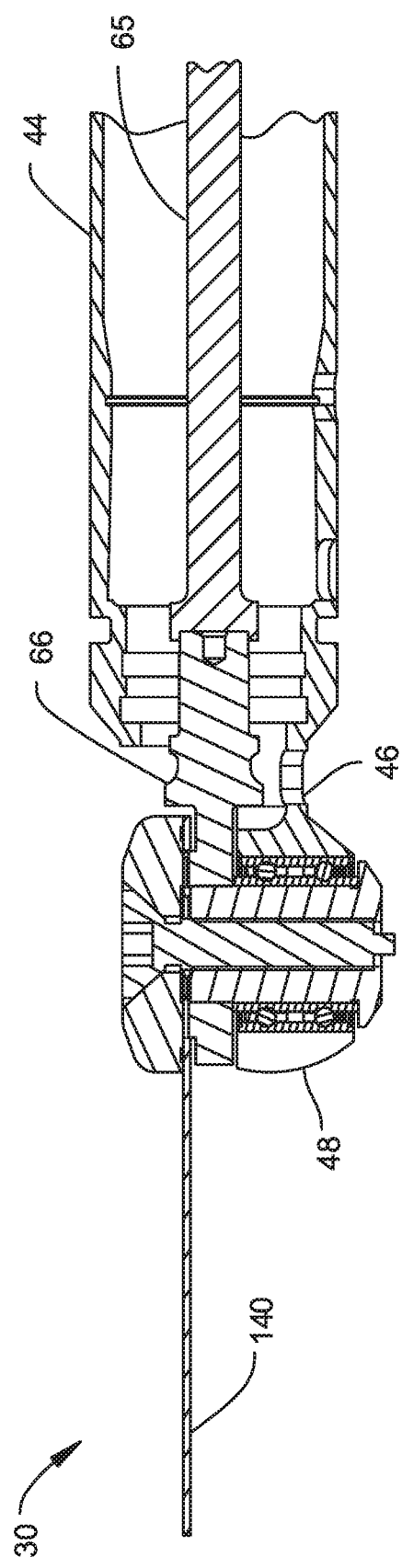
FIG. 2 is a cross sectional view of the saw assembly.

FIGS. 1 and 2 depict a surgical saw assembly 30 constructed in accordance with this invention. Saw assembly 30 consists of a saw unit 40 and a blade 140. The depicted saw assembly 30 is what is referred to as a micro sagittal saw. This saw is used to perform procedures on small bones. Examples of bones on which a micro surgical saw is used to perform surgery on include: the skull; the spine; the hand; and the foot. Internal to the saw assembly 30 is a motor 62 represented by a phantom cylinder. Motor 62 includes a rotating shaft 64 represented by a smaller diameter phantom cylinder. The actuation of the motor 62 results in the back and forth oscillations of the blade 140. More specifically, the blade 140 pivots back and forth around an axis that extends through the plane of the blade.

Saw unit 40 includes a saw body or shell 42, seen best in FIGS. 2 and 3, that houses or holds the other components of the saw unit. Body 42 has a generally cylindrical main section 44. Body main section 44 is dimensioned to be held in the hand. Typically, the saw body 42 is held between the thumb and forefinger or between the thumb and middle finger. Extending distally forward of the main section, the saw body 42 has a neck 46. ("Distally" is understood to mean away from the surgeon; towards the site on the patient to which the blade 140 is applied. "Proximally" is understood to be towards the surgeon holding the saw unit 40; away from the site on the patient to which the blade 140 is applied.) The saw body 42 is dimensioned so that the neck 46 is, in planes perpendicular to the proximal-to distal longitudinal axis along the body, generally semi-circular in cross section. Saw body 42 is further dimensioned so that the outer surface of the neck 46 is located radially inward from the outer surface of the body main section 44. Forward of and integral with the neck 46, the saw body 42 has a head 48. In the depicted version of the invention, head 48 has a shape of a slice section of a sphere. More particularly, saw head 48 has a shape in which a first surface is along a plane that extends slightly above the mid-plane of the sphere. A second surface that is parallel to the first surface is located closer to what would be one of the poles of the sphere defined by the head 48. Saw body 42 is further shaped so that the head 48, relative to the longitudinal axis through the body 42, extends outwardly of the neck 46.

Figure 4:
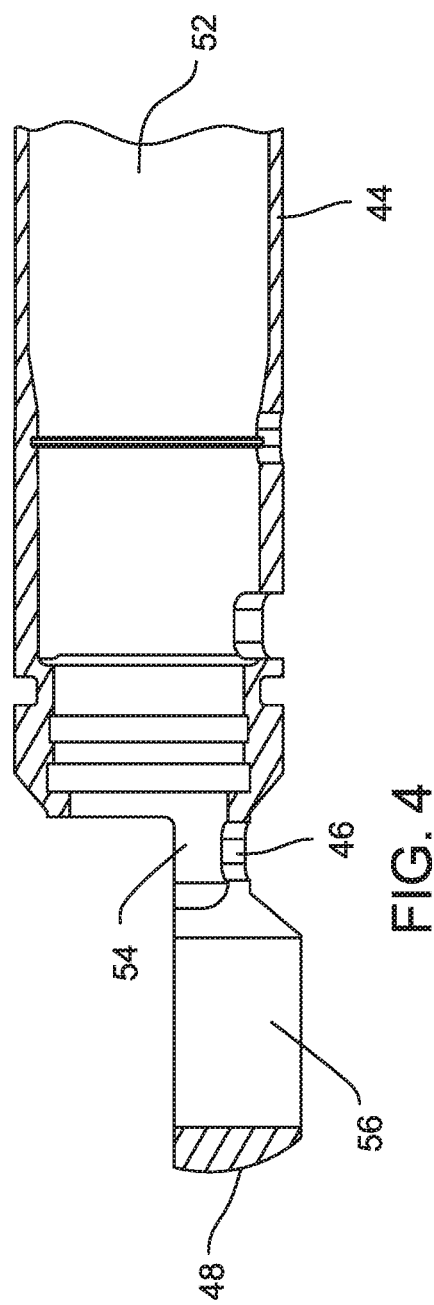
FIG. 4 is a cross sectional view of the distal end of the body of the saw unit of this invention including the head and neck.

The saw body 42 is further formed so there is void space 52 internal to the body main section 44 as seen in FIG. 4. The distal end of the body main section 44, has an opening, opening not identified. Saw body 42 is further formed so there is a recess 54 in the neck 46. Owing to the opening in the distal end of the body main section 44, body void space 52 and recess 54 are contiguous. Saw body 42 is further formed so that saw head 48 has a bore 56 that extends through the head. The saw body 42 is formed so that bore 56 extends along an axis perpendicular to the longitudinal axis through the body. The distal end of recess 54 opens into bore 56.

Returning to FIG. 1 it can be seen that motor 62 is disposed in void space 52 internal to the body main section 44. Motor 62 is often electrically driven. A cable 60 extends proximally from the proximal end of the body 42. Cable 60 is connected to a control console not illustrated and not part of the present invention. The control console supplies energization signals over cable 60 to the motor 62 that actuate the motor. Not shown are the connections between the individual conductors internal to the cable 60 to the motor 62.

A drive link 66, seen best in FIGS. 2, 3 and 5, is pivotally mounted to the saw body head 48. The drive link 66 includes a cylindrical stem 68. Forward of stem 68, the drive link 66 has a head 70 that is approximately disk like in shape. More specifically, drive link head 70 has two opposed surfaces 72 that are planar and parallel. In FIG. 5, one surface 72 is fully illustrated and the edge of the opposed surface 72 is called out. The perimeters of surfaces 72 are generally circular in shape. The outer diameter of the head 70 is generally equal to the outer diameter of the widest portion of body head 48. In the depicted version of the invention, the distal end of body head 48 is truncated. Thus, the most distally directed surface of the head 70 is a flat 76. Flat 76 is present for manufacturing reasons and is otherwise not relevant to this invention.

The drive link 66 is further formed to have a hole 77 that extends between the link major surfaces 72. Hole 77 is circular in shape and is concentric with the axis of the link head 70 that extends between the major surfaces 72. The drive link 66 is further formed to have four arcuate islands 78, two islands identified, that extend upwardly from the head major surface 72 that is directed away from saw body head 48. The islands 78 are located adjacent the outer perimeter of hole 77 and are arcuately shaped. Each island 78 is arcuately spaced from the adjacent islands 78. Thus, between each pair of islands 78 there is an island void, i.e., a channel 80, (two channels identified).

A pivot pin 84 and a bearing assembly 92 rotatably hold the drive link 66 to the body head 48. The pivot pin 84, as seen in FIGS. 6 and 7, has an elongated cylindrical stem 86. Stem 86 is dimensioned so that the top of the stem, as seen in FIG. 3, can be press fit or otherwise secured in the hole 77 formed in the drive link head 70. The components forming the saw unit 40 are further dimensioned so that the pin stem 86 has a diameter less than the diameter of the saw body head bore 56. Pin 84 is further formed so that at the end of the stem 86 opposite the end fitted to the drive link 66 there is head 88. Pin head 88 extends radially outwardly from the stem 86. The pivot pin 84 is formed with an axially extending through bore, bore 89. Bore 89 extends from the top of the pin stem 86, the portion of the pin fitted to the drive link 66 to and through the pin head 88. While not seen it should be understood that the cylindrical inner wall of pivot pin 84 that defines bore 89 is threaded.

Bearing assembly 92, seen best in FIG. 8, includes sleeve shaped inner and outer races 94 and 98, respectively. Inner race 94 is dimensioned to have a tight slip fit over pin stem 86. Outer race 98 is dimensioned to have a press fit against the inner cylindrical wall of the body head 48 that defines bore 56. It is further noted that races are dimensioned so that the inner race 94 extends above and below the outer race 98. Two rings of ball bearings 96 provide the rotating interface between the races 94 and 98. Not identified are the grooves in the surfaces of the races 94 and 98 in which the ball bearings 96 are seated.

When saw unit 40 is assembled, bearing assembly 92 rotatably holds pin 84 and, by extension, drive link 66 to the saw body head 48. The components are dimensioned so that inner race 94 protrudes both above and below saw body head 48. The drive link major surface 72 directed towards saw body head 48 is disposed against the section of the inner race 94 that projects above the head 48. Pin head 88 is disposed against the section of the inner race 94 that projects below the saw body head 48.

A linkage assembly, represented by a bar 65 in FIG. 2, extends from the motor shaft 64 to the drive link stem 68. This linkage assembly transfers the rotational motion of the motor shaft 64 into motion that causes the drive link 66 to oscillate back and forth. More specifically, when motor 62 is actuated, the linkage assembly causes the drive link 66 to oscillate back and forth around the top to bottom longitudinal axis through pin 84. The structure of the linkage assembly is not part of the present invention.

A cap 102, seen best in FIGS. 9 and 10, is moveably mounted to the saw body 42 above the exposed major surface of drive link 66. Cap 102 is generally circular in shape. The cap 102 is formed with a through hole 106 that extends top to bottom through the cap. Hole 106 is concentric with the top-to-bottom axis through the cap. The top of the cap 102 is further formed to have a tapered opening 104 that leads into hole 106.

The bottom of the cap 102 is formed with a planar undersurface 112. Three sets of arcuately shaped feet extend downwardly from undersurface 112. These feet include the press feet 114 and stop feet 118 that are interleaved in a common circle. Feet 114 and 118 are arcuately spaced apart from each other. The saw unit 40 is constructed so that each press foot 114 is located over a separate one of the channels 80 of the underlying drive link 66. The components are constructed so that each press foot 114 subtends an arc that is less than the arc of the underlying drive link channel 80. Each stop foot 118 subtends an arc greater than the arc subtended by a single press foot 114. The components forming the saw unit 40 are further constructed so that the arc separating adjacent stop feet 118 is greater than the arc of the drive link channel 80 located between and below the adjacent stop feet. Internal to this arc between adjacent stop feet 118 is one of the press feet 114 located between each pair of adjacent stop feet 118 Stated another way, each stop foot 118 is located above an underlying drive link island 78. Each stop foot 118 subtends an arc less than the arc subtended by the underlying island 78. Given that the arcuately adjacent feet 114 and 118 are spaced from each other, there is a gap 116 between the adjacent feet. Owing to the dimensioning of the drive link islands 78 and cap feet 114 and 118, each gap 116 is partially located above an underlying end section of one of the drive link channels 80. The remainder of each gap 116 is located above one of the drive link islands 78 that defines the perimeter of the channel.

The third set of feet of the cap 102 are arcuately shaped compress feet 120. Compress feet 120 also extend downwardly from the cap undersurface 112. The compress feet 120 are spaced radially outwardly and apart from the circle of press and stop feet 114 and 118, respectively. In terms of arcuate slice sections of the cap 102, each compress foot 120 is in registration with a separate one of the press feet 114 or one of the stop feet 118. Each compress foot 120 subtends the same arc as the foot 114 or 118 with which the foot 120 is in registration. Each compress foot 120 is arcuately spaced apart from the adjacent compress feet 120. Feet 114, 118 and 120 all extend down the same distance from cap undersurface 112.

A screw 122 and knob 134, seen best in FIG. 3, control the relative height of the cap 102 to the drive link 66. Screw 122 has a head 124 dimensioned to seat in the tapered opening 104 of cap 102. A shaft 126 extends downwardly from the head 124. Shaft 126 is formed with threading (not illustrated). Shaft 126 is dimensioned to extend through the hole 106 internal to cap 102 and the bore 89 formed in pivot pin 84. The screw shaft threading is engaged with the threading around the pivot pin bore 89. A short cylindrical foot 128 projects from the end of the shaft 126 opposite screw head 124. Foot 128 has a diameter less than that of the screw shaft 126. When saw unit 40 is assembled, foot 128 projects a short distance below the pivot pin 84.

Knob 134, seen only in FIGS. 1 and 3, is attached to screw foot 128. The knob 134 is thus located below the head 48 of the saw body 42. The knob 134 rotates the screw 122. The component to which the screw 122 is attached, the pivot pin 84, is held static to the drive link 66. Therefore, the rotation of the screw by the knob 134 results in the raising and lowering of the screw head 124 relative to the drive link 66.

The blade 140 of saw assembly 30 of this invention, as seen in FIGS. 11 and 12, is a single piece assembly. Blade 140 is shaped to have a body 148 that is generally planar in shape. At the proximal end of the body the blade has a foot 142. Foot 142 is rounded in shape and has a diameter that is greater than the width of the more distal portions of the blade body 148. The outer diameter of the foot 142 is substantially equal to the common diameter of the drive link head 70 and cap 102. A slot 144 extends forward from the proximal end of foot 142. Slot 144 has a width that allows the slot to receive screw shaft 126. The blade 140 is further formed so that slot 144 opens up into a hole 146 that extends through the opposed planar faces of the blade foot 142. Hole 146, exclusive of any lock tooth 150 disposed therein, is circular in shape and has a diameter greater than the width across slot 144 that defines a perimeter portion.

Blade 140 is further formed to have lock teeth 150 that extend inwardly from the portion of the foot that defines the outer perimeter of hole 146. Each lock tooth 150 has a body 152 that is approximately in the shape of a truncated isosceles triangle. The bodies 152 of the lock teeth have the same top to bottom thickness T1 as the top to bottom thickness T2 of the blade body 148. The thickness T1 across each body 152 of each tooth 150 may generally decrease as the tooth extends inwardly toward the center of the hole. The portions of the teeth 150 closest to the center of hole 146 are rounded to define a circle that is concentric with the hole. A wing 154 projects, i.e., extends, arcuately outwardly from the each of the opposed side surfaces of the tooth body 152. Each wing 154 is formed from two opposed tapered surfaces. Thus, the thickness T1 across opposed faces of the body 152 of a lock tooth 150 is generally constant along the tooth body 152. The thickness T3 of each tooth wing 154 decreases along lines perpendicular to the line along which the tooth body 152 extends inwardly towards the center of hole 146. In the illustrated version of the invention, the radially outermost portion of each tooth wing 154 is spaced inwardly from the perimeter edge of the foot that defines the outer perimeter of hole 146. Given that each wing 154 is spaced from the adjacent perimeter of foot 142, it should be appreciated there is a tooth void space 156 between the foot and the wing. The components forming the saw assembly 30 of this invention are further dimensioned so that the parallel faces of the tooth bodies 152 have a side-to-side width that is both less than the width across a channel 80 formed in the drive link and greater than the width across a press foot 114 integral with the cap 102.

The blade 140 is further formed so that cutting teeth 158 extend forward from the distal end of the blade body 148. Cutting teeth 158 are designed to, when the blade 148 is oscillated, remove the tissue against which the teeth 158 are applied. The geometry of the cutting teeth 158 is not part of the present invention.

While blade 140 is a single piece assembly, there are differences in the characteristics of the features of the blade. More specifically, the lock teeth 150 are formed from material that is relatively soft, relatively ductile. This material typically, but not always, has a maximum hardness in the Rockwell B Range. The blade body 148, including cutting teeth 158, are formed from material harder than the material from which the lock teeth 150 are formed. Typically, the blade body and teeth are typically, but not always, formed from material that has a hardness in the Rockwell C Range.

One means of so fabricating the blade is to form the whole of the blade, the foot 142, the body 148, the lock teeth 150 and the cutting teeth 158 out of a single piece of hard metal. After the blade is so shaped, the lock teeth 150 are subjected to a further processing to soften the teeth 150, increase their ductility. In one such process, the blade is formed from stainless steel. Once the blade 140 is formed, the lock teeth 150 are subjected to a localized annealing process. For example, the lock teeth 150 can be so annealed by directed a laser beam to the surface of the teeth. The photonic energy of the laser beam heats the teeth 150 to their annealing temperature. Once the lock teeth 150 are heated to the annealing temperature, the lock teeth are allowed to cool at a relatively slow rate. Often the cooling is at a controlled rate. Given that the relatively low thermal conductivity of the stainless steel, the heat generated by this remains localized. The heat does not therefore result in the undesired softening of the remainder of the blade 140. As a result of this annealing process, the metal forming the lock teeth 150 becomes softer, more ductile, than the material forming the rest of the blade 140.

Figure 11A:
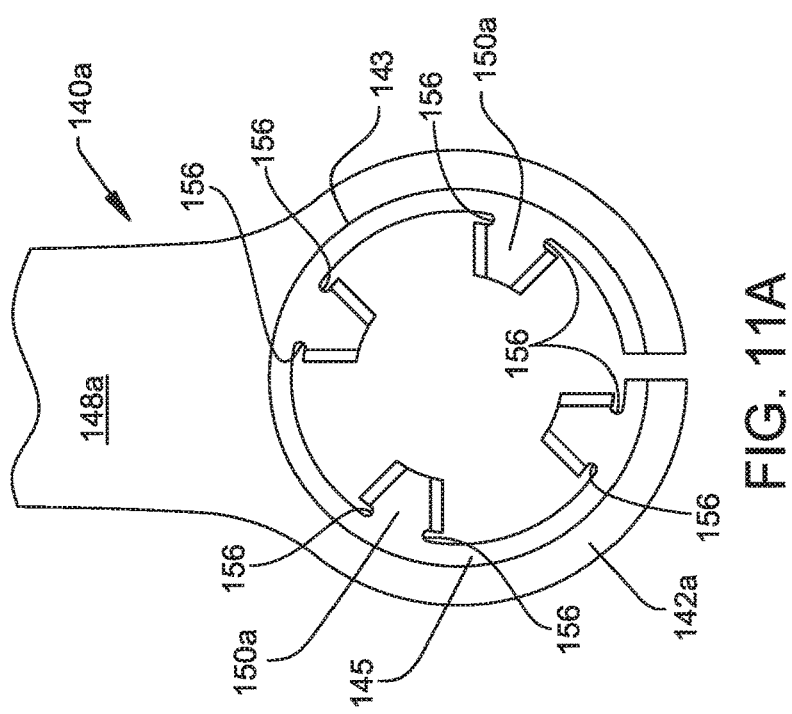
FIG. 11A is a plan view of an alternative construction of the blade of this invention.

A second means to so form the blade is described with reference to FIG. 11A. The blade 140a, is formed with a body, in FIG. 11A, body 148a, including the foot 142a and cutting teeth (not seen) out of the relatively hard material. Foot 142a is formed with a through hole 143. A washer like member 145 formed from more ductile material is welded or otherwise secured to the through hole formed in the foot 142. This washer like member 145 is formed to have the blade lock teeth 150a.

A saw assembly 30 of this invention is readied for use by coupling the blade 140 to the saw unit 40. To prepare for this operation, knob 134 is rotated to cause screw head 124 to move to the position where the screw head is spaced from the drive link 66. This allows cap 102 to be likewise be moved upwardly away from the drive link 66. When the saw unit 40 is in this state, the saw unit is in the load or unlocked state.

Figure 13:
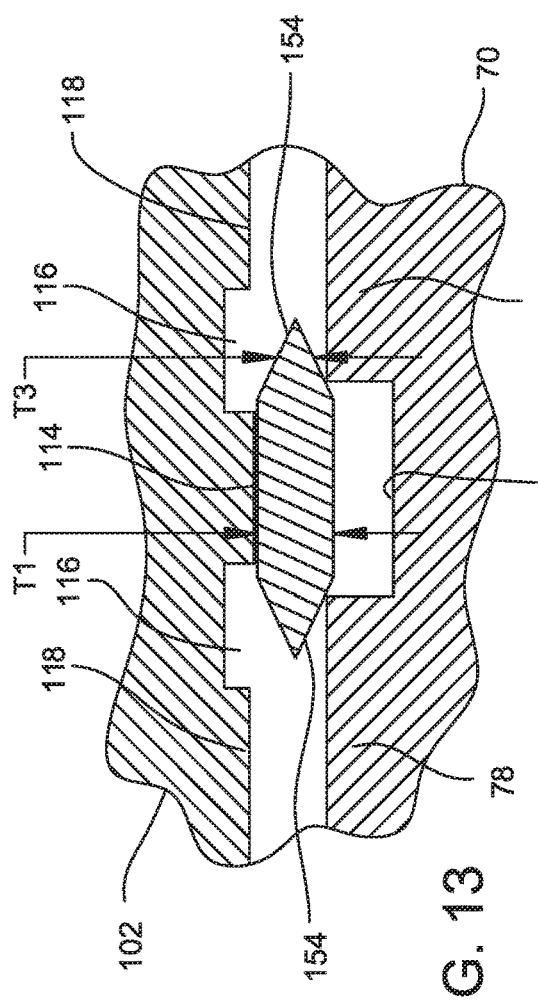
FIG. 13 is a cross sectional view depicting the relative location of the saw unit anvil and press and the saw blade prior to the locking of the blade.

Once the saw unit 40 is in the unlocked state, the cap 102 is moved away from the drive link 66 a sufficient distance, blade foot 142 is seated between the drive link head 70 and the underside of the cap 102. The presence of slot 144 in the blade foot 142 facilitates the insertion of the blade around screw 122. The saw unit and blade are placed in registration with each other as seen in FIG. 13. The blade lock teeth 150 are seated over the channels 80 formed on the drive link head 70 so that each the wings 154 of each tooth 150 rest on the edges of the adjacent and spaced apart islands 78. Thus, the portion of the tooth 150 between the wings 154 is thus disposed in the channel 80 between the islands 78. The cap 102 is positioned so that each press foot 114 is disposed over the face of the tooth body 152 opposite the face that is disposed in the underlying drive link channel 80.

Figure 14:
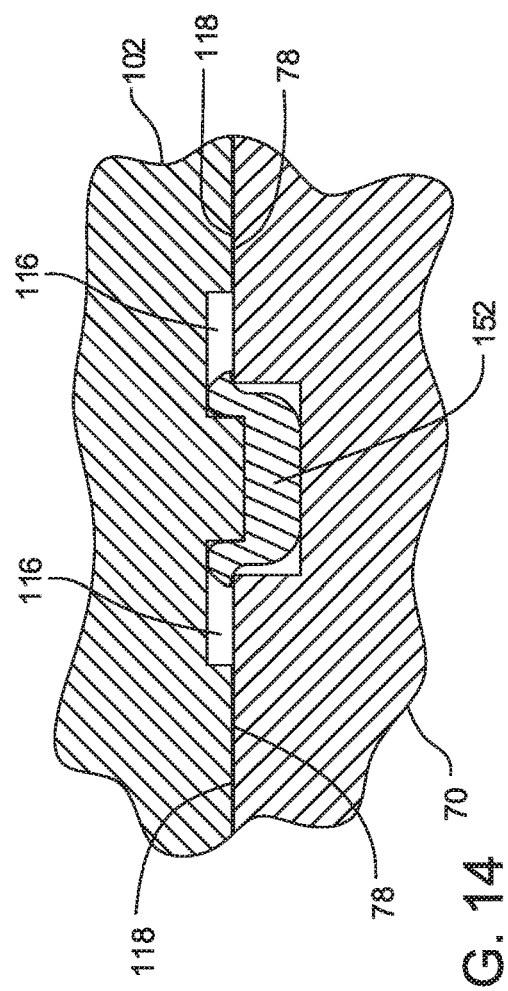
FIG. 14 is a cross sectional view depicting how, when the blade is locked, a blade locking tooth is deformed, coined, by the anvil and press.

Once the components of saw assembly 30 are so aligned, knob 134 is rotated to place the saw unit 40 in the run or locked state. Specifically, the knob 134 is rotated to lower screw 122 and, by extension, cap 102. As the cap 102 is lowered, the press feet 114 press against underlying blade lock teeth 150. Since the drive link 66 is static, the drive link head 70, including islands 78 function as a static anvil. Cap 102, having press feet 114, functions as a press. Owing to the ductile nature of the lock teeth 150, the movement of the press feet towards the drive link results in the teeth deforming between the drive link and the cap. As seen by reference to FIGS. 14 and 15, the overlying press foot 114 presses against the tooth main body to push the tooth into the underlying channel 80 in the drive link. In FIG. 15, the perimeters of feet 114, 118 and 120 are depicted as dashed lines. Cap 102 thus functions as the press and the faces of the press feet 114 are thus the press surfaces of the cap 102. The movement of the press feet 114 causes the tooth wings 154, which are thinner than the adjacent tooth main body 152, to bend around the edges around the perimeter of the islands 78. Once the locking teeth 150 seat against the underlying portion of the link main surface that defines the bases of the channels 80, the continued motion of the press feet causes the portions of the teeth main body adjacent the edges of the press feet to bend around these edges. Thus, as seen in FIG. 14, the wing portions 154 of each tooth as well as a small sections of the tooth body 152 adjacent the wings moves are bent into the gaps 116 between the press feet 114 and the adjacent stop feet 118.

Cap 102 is lowered against the drive link until the stop feet 118 abut the underlying islands 78 integral with the drive link 66. In FIG. 15, to minimize confusion, the islands 78 against which feet 118 abut are not shown. Once the cap 102 is so positioned, the saw unit can be considered in the run or locked state.

A further effect of the lowering of cap 102 is that, as seen in FIG. 15, the compress feet 120 bear against the blade foot 142. As a consequence of the press feet 114 pushing the locking teeth 150 into the channels 80 and the compress feet 120 pushing against the blade foot 142, the blade foot is pushed against circular section of the drive link major surface 72 located radially outwardly of islands 78. The blade foot 142 is thus compressed by the drive link major surface 72 and the opposed cap compress feet 120.

As a result of the locking of the blade 140 to the saw unit 40, the blade foot 142 is more than compressed between the drive link 66 and cap 102. The deformation of the blade lock teeth 150 around the adjacent components of the drive link and cap essentially make the drive link, the cap and the blade a single piece assembly. There is no clearance between the drive link 66 and the saw blade 140. When the drive link 66 is oscillated, blade 140 oscillates as one with the drive link 66. There is essentially negligible, if any, movement of the blade 140 relative to the drive link and cap. The undesirable effects associated with saw unit components 66 and 102 and the blade 140 moving relative to each other are essentially eliminated.

These undesirable effects include the movement of the blade relative to the saw that can adversely affect the precision of the cuts made be the blade. Still another undesirable effect that is essentially eliminated is the wear on the saw unit that results from the blade slap. A further undesirable effect this invention reduces if not eliminates is the frictionally induced heating that can occur as a result of the movement of the blade relative to the saw unit. Furthermore, since the blade 140 for all intents and purposes moves in unison with the saw coupling assembly, during each phase of an oscillatory cycle, the blade undergoes essentially the same arcuate sweep as the coupling assembly. This ensures that, in each sweep a tooth of the blade will sweep to at least the location of the adjacent tooth at the start of the sweep. The sweeping of the tooth along this arc increases the likelihood that, in the sweep all the bone between the teeth was, in the sweep sheared away. The removal of all this bone in a single sweep can enhance the efficiency of the cutting process.

A further advantage is due to the fact that, because the blade 140 is firmly attached to the coupling assembly, there is little, if any, whip, oscillation of the blade outside of the plane of the cut. This means that when the blade is initially applied against bone, the blade can be used to form an initial cut that is thinner than the cut that is sometimes formed when the blade engages in whip motion. Since this initial cut is thinner, the surgeon can use a blade that is thicker than the blade the surgeon may otherwise use to form the cut. A benefit of using this thicker blade is that this blade will inherently be stiffer than a thinner blade. This is beneficial because as the blade is advanced deeper into the bone the stiffness of the blade reduces the extent to which any blade flexure adversely affects the precision of the cut.

Another feature of this invention is that blade is not only compressed between the drive link and the press feet 114. The blade is also compressed between the drive link major surface 72 and the cap compress feet 120. This substantially reduces the likelihood that, if the press feet and drive link fail to collectively hold the blade lock teeth 150 to the saw unit 40, the blade will rapidly work free of the saw unit.

A further benefit of this invention, is that blades of different thicknesses can be clamped between the drive link 66 and the cap 102. The primary design criteria in providing a saw unit of this invention able to accept these different blades is that the screw should allow the cap to move above the blade a sufficient height so a blade having the largest thickness for use with the saw unit can be inserted between the drive link and the cap.

Figure 16:
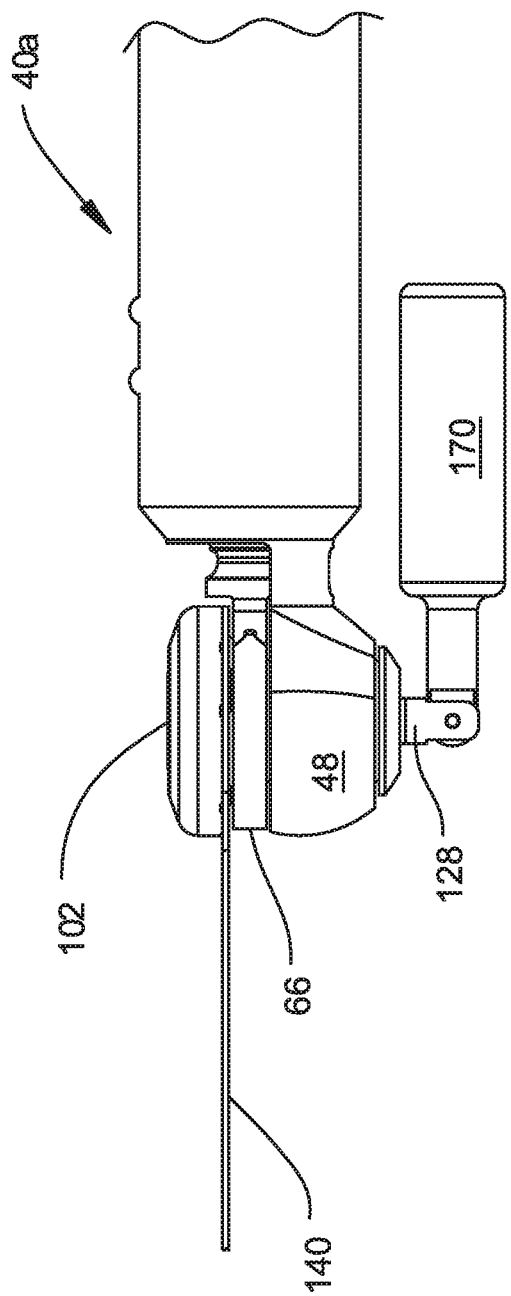
FIG. 16 is a side view of an alternative saw unit of this invention.

FIG. 16 is directed to an alternative saw unit 40*a* of this invention. The majority of the components of saw unit 40*a* are identical to the components of first described saw unit 40. These components are not redescribed. Instead of being provided with a knob to raise and lower screw 122, saw unit 40*a* has an arm 170. Arm 170 is pivotally attached to the foot 128 integral with the screw 122.

This construction of the invention has a further benefit by selective forming the pitch of the threading integral with pivot pin 84 and screw 122. Specifically, the saw unit 40*a* can be constructed so that the orientation of the arm relative to the saw body 42 serves as an indicia regarding whether or not the saw unit is in the fully locked/run state. For example, in some versions of the invention, the components can be arranged so that when the saw unit 40*a* is so locked arm 170 is parallel with the longitudinal axis of the saw body 42.

In more preferred versions of this construction of the invention, the orientation of the arm 170 serves as both an indication of the run or load state of the saw unit 40*a* and the type of blade 140 mounted to the saw unit. For example in some versions of the invention, when a blade that has a relatively large top face (e.g., face 186) to bottom face (e.g., face 182) thickness T2 is fully locked to saw unit 40*a* the arm 170 is both parallel to the longitudinal axis of the saw body 42 and is pointed distally forward. When a blade with a relatively thin top face (e.g., face 186) to bottom face (e.g., face 182) thickness T2 is fitted to the saw unit 40*a*, an extra half turn or one and half turns of the screw may be needed to lock the blade. When such a blade is so mounted, the arm 170 will be aligned with the longitudinal axis of the saw body 42 and point proximally rearward.

It should be understood that if the arm 170 points forward when the saw is initially placed in the lock state, the arm 170 may extend below the blade 140. This could require the pivoting of the arm proximally rearward to ensure the full insertion of the blade.

Figure 17:
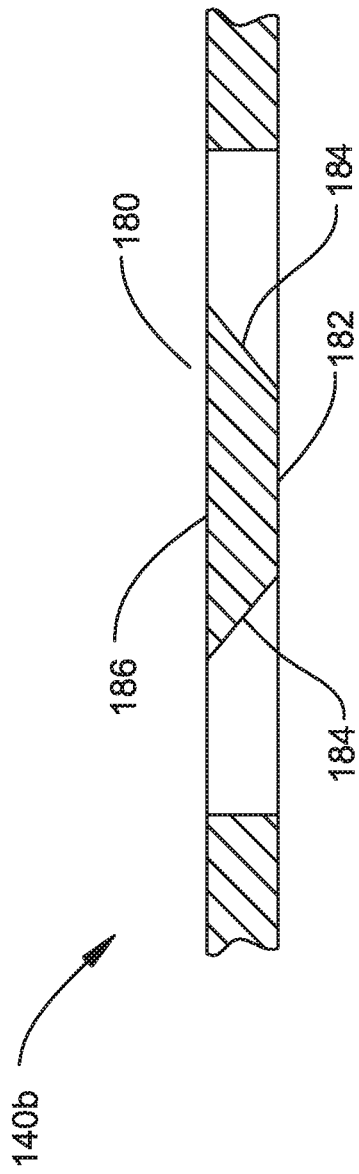
FIG. 17 is a cross sectional view of the blade locking tooth of an alternative blade of this invention.

FIG. 17 depicts a portion of an alternative blade 140*b* of this invention. Blade 140*b* contains many of the same features of blade 140. To avoid redundancy these features are neither redescribed nor again illustrated. The difference between blades 140 and 140*b* concerns the shape of the locking tooth. Blade 140*b* has lock teeth 180, one of which is seen in cross section in FIG. 17. In cross section, a lock tooth 180 can be considered trapezoidal in shape. The tooth 180 has opposed parallel lower and upper, i.e., bottom and top, faces 182 and 186, respectively. Lower face 182 is shorter in length than upper face 186. Tapered side surfaces 184 extend upwardly from the opposed ends of the lower face. Side surfaces 184 extend to the ends of the adjacent upper face 186. The teeth 180 are formed so the opposed side surfaces of each tooth are symmetric. Side surfaces 184 and outer sections of upper face 186 opposed to the side surfaces thus form the outer surfaces of the wings of lock tooth 180.

A benefit of blade 140*b* over blade 140 is that it may be more economical to provide a blade with teeth 180 than with teeth 150. When blade 140*b* is provided, care must be taken to ensure that the blade is orientated so that the teeth bottom surfaces seat in the channels 80 between drive link islands 78.

The foregoing is directed to specific versions of the invention. The invention may have features different from what has been described.

For example, the features of the different versions of the invention may be incorporated together.

Further, while the described saw of this invention is a sagittal saw, this invention is not limited to sagittal saws. This invention may be employed as part of reciprocating surgical saw. A reciprocating surgical saw consists of a saw unit and complementary blade that are arranged so that when the saw unit is actuated, the blade moves back and forth along a path of travel identical or close to being parallel to the longitudinal axis of the blade. The saw assembly of this invention may also be constructed as an oscillating saw. An oscillating saw is a saw designed to pivot a blade around an axis that extends along the axis of the saw unit. For the purposes of this invention, since each of the blades repetitively move back and forth, the saw that so cycles the blade is consider to reciprocate the blade back and forth. Another version of the saw unit of this invention is an acetabular cup remover. An acetabular cup remover, as implied by its name, is a specialized saw used to remove a previously implanted artificial acetabular cup. For the purposes of this invention, since each of the blades is repeatedly cycled back and forth, the saw that so cycles the blade is consider to reciprocate the blade back and forth.

Just as this invention is not limited to a particular type of saw, the saw unit is not limited to saw units having electrically powered motors. In alternative versions of the invention, the motor may be a hydraulically or pneumatically driven motor or actuator. If the saw unit includes an electrically driven motor or actuator, it may be possible to attach a battery to the saw unit in order to provide the current needed to actuate the motor.

The described saw unit 40 of this invention is a micro sagittal saw. This saw assembly of this invention may be part of what is referred to as a heavy duty surgical saw. A heavy duty surgical saw is designed to remove large sections of tissue such as the bone of the leg. This is the type of saw disclosed in the previously incorporated by reference U.S. Pat. No. 8,100,912/PCT Pub. No. WO 2007/011542. Often a heavy duty surgical saw unit looks different than the elongated saw unit of FIG. 1. More specifically, a heavy duty surgical saw is often pistol shaped. The saw has a handgrip and barrel that typically extend forward from the handgrip. The motor is disposed in the handgrip or the barrel. The saw head extends forward from the distal end of the barrel.

The various assemblies of this invention may vary from what has been described. For example, the clamping assembly that urges the press feet the anvil may not always include a threaded screw. In some versions of this invention, a rod able to move relative to the head of the saw unit performs this function. The rod is moved between the run and load positions by a manual actuating caroming system. The Applicant's U.S. Pat. No. 7,704,254/PCT Pub. No. WO 2007/030793, the contents of which are incorporated herein by reference disclose how a rod may be so mounted to a saw head. In some versions of the invention, the assembly that moves the press against the anvil may not have a moving component that extends through the blade. Thus, in some versions of the invention, the press may be a plate located over the face of the blade opposite the face directed to the anvil. One or more linkage members located around the outer surface of the blade connect the press plate to the rest of the saw unit. These linkage members are actuated to urge the plate against the blade (into the run position) or away from the blade (into the load position).

In some versions of the invention the components forming the anvil and press are formed with complementary features to facilitate the registration of these components when the saw head is moved between the locked and load states. For example, one of the cap or the drive link may be provided with a pin. The other of the drive link or cap is provided with a bore for receiving the pin. The seating of the pin in the bore ensures the registration of the cap feet to the underlying anvil of the drive link.

Further, there is no requirement that, relative to gravity reference, the press feet, when moving towards the blade and the anvil move downwardly in the plane of gravity. In some versions of the invention, when the press feet are moved towards the blade and anvil, the member that includes the press fit may move in any direction relative to gravity reference plane. Thus while in the primary version of this invention the press feet carrying press is a cap, it is understood that this press may not always be located above the anvil. In alternative constructions of the invention, this press, relative the gravity reference plane be located to the side or below the anvil.

It should likewise be understood that the anvil and press of this invention may have alternative constructions. For example, there is no requirement that in all versions of the invention, the press be provided with compress feet that function as the backup features to hold the blade to the saw unit. In some versions of the invention either one of the anvil or press is provided with protruding features. The complementary blade is provided with both the lock teeth and through openings. When the blade is mounted to the saw unit, the blade is positioned so that the protruding features associated with the saw unit seat in the openings formed in the blade. The seating of the protruding features in the blade functions as the backup assembly that substantially eliminates the likelihood that the blade can work free of the saw unit. In some versions of the invention, the saw unit and blade do not have any features that provide a redundant lock of the blade to the saw unit.

It is similarly within the scope of this invention that the saw unit have components analogous to the compress feet but no components similar to the stop feet. In some versions of the invention, components functionally equivalent to both the stop feet and the compress feet may be omitted. In some versions of the invention, a press foot and a compress foot may be different sections of a single component. In some versions of the invention, a stop foot and a compress foot may be different sections of a single component.

Some saw units and blades of this assembly may be provided so that when the saw unit press feet coin the blade lock teeth, the press feet partially or fully penetrate a portion of the lock teeth. It is further contemplated that in most versions of the invention the blade will have plural deformable lock teeth and the saw unit has one or more features able to deform these teeth. However, it is also within the scope of this invention that the blade have a single deformable lock tooth and the saw unit has a single press foot for deforming the lock tooth. Likewise, while often preferable, there is no requirement that in all versions of the invention, that the press deforms the lock teeth so that the teeth, when deformed, abut the underlying base surface of the anvil. In FIG. 14 these are the portions of major surface 72 that defines the bases of channels 80.

Variations in the blade of this invention are also possible. For example, it should be understood that this invention is not limited to the disclosed feature of where the blade lock teeth are arranged around a circle. FIG. 18 illustrates an alternative blade 202 of this invention. Blade 202 is a reciprocating saw blade. Blade 202 has a body 204 with opposed proximal and distal sections 206 and 208, respectively. The blade 202 is formed with cutting teeth 228 that extend outwardly from a side surface of the blade distal section 208.

Plural lock teeth 210, 214 and 218 extend from the opposed sides of the blade proximal section 206. Lock teeth 210, 214 and 218 thus extend outwardly from the perimeter edges of the blade body. In the illustrated version of the invention the lock teeth 210, 214 and 218 are symmetrically arranged around the proximal to distal longitudinal axis along the blade body 204. Lock teeth 210, 214 and 218 are more ductile, more prone to deformation, when a force is applied then the blade body 204, especially the portion of the body that defines the cutting teeth 228.

Each lock tooth 210, 214 and 218 has a main body 220, only two identified. At least one tapered wing extends outwardly from the main body of each lock tooth 210, 214 and 218. In the illustrated version of the invention, a single tapered wing 212 extends distally forward from the body of each lock tooth 210. Two tapered wings 216 extend outwardly from the opposed sides of each lock tooth 214. A single tapered wing 222 extends proximally from the side of each lock tooth 218. It should be understood that FIG. 18 illustrates another feature of this invention, there is no requirement that each lock tooth have two opposed tapered wings. Blade 202 further illustrates another aspect of this invention. Specifically, blade 202 is further designed so that the outer edges of the tapered wings of the lock teeth are parallel to the outer edges of the bodies of the lock teeth from which the wings extend. In some versions of the invention, the lock teeth may be shaped so that extending away from the section of the perimeter of the blade from which the teeth extend, the edges of the tapered wings extend outwardly from the adjacent tooth body.

Likewise, it should be appreciated that there is no requirement that in all versions of the blade the lock teeth project outwardly from the more proximal sections of the blade body. Similarly, in versions of the invention where the blade has a foot with inwardly projecting lock teeth, the foot may have a width less than the width of the more distal sections of the blade body. Likewise, the lock teeth may be arranged to project proximally into space adjacent the proximal end of the blade.

Further, it should be understood that in some versions of the invention, one or more of the lock teeth may not have tapered sections. In some versions of the invention the wing portions of the teeth may simply be thinner in cross sectional thickness than the portion of the tooth bodies from which the wings extend. In some versions of the invention, the lock teeth may be of constant cross sectional thickness along the whole of the teeth. Likewise, in some versions of the invention, the top to bottom thickness of the blade lock teeth may not equal the top to bottom thickness of the blade body. In many versions of the invention, the blade locking teeth may be thinner than the blade body. There can be versions of the invention wherein the thickness of the blade locking teeth is greater than that of the blade body.

Saw blade 202 is further designed so that lock teeth wings 212, 216 and 220 are spaced away from the perimeter edge of the portion of the blade body 204 from which the bodies of teeth 210, 214 and 218 extend. Thus there is a tooth void space 219, a gap, between each wing and the adjacent perimeter of the blade body. It should be understood that spacing of the wings away from the perimeter of the blade body minimizes the force needed to deform, coin, the wings when the anvil and press are brought together. It is within the scope of this invention that in some versions of the blade the reduced cross sectional thickness portions of the lock teeth extend from the perimeter portions of the associated blade bodies. In some embodiments of these versions of the invention, the one or more lock teeth do not have section of constant thickness. Thus, in some versions of the invention, there is no break, no separation, between one or more of the lock teeth and the adjacent perimeter portion of the blade body from which the teeth extend.

Likewise, it is within the scope of this invention that blade will have lock teeth having different shapes and or dimensions. For example, there is no requirement that in all versions of the invention the lock tooth (or teeth) project outwardly of the adjacent edge of the blade body. FIG. 19 illustrates another sagittal saw blade 246 of this invention. Blade 246 includes a body 250. The body 250 has a proximal section 258 and a distal section 260 located forward of the proximal section. Body distal section 260 has a side-to-side width greater than that of the proximal section 258. Cutting teeth 262 extend forward from the body distal section 260.

Blade body 250 has a single lock tooth 252. Lock tooth 252 is generally U-shaped. The lock tooth 252 is formed so as to have a base section 254 integral with and located immediately proximal to the proximal end of the body proximal section 258. The base section 254 of the lock tooth 252 thus forms the proximal end of the blade 246. Two arms 256, also part of lock tooth 252, extend distally forward from the opposed ends of the base section 254. The perimeter of each arm 256 integral with the lock tooth 252 is flush with perimeter of the portion of the base proximal section 258 immediately forward of the arm.

The lock tooth 252 may be shaped to have an outer perimeter section 257. The outer perimeter section 257 of the tooth 252 has a thickness less than that of the section of the tooth 252 located inward of the perimeter section. In some versions of the invention, this perimeter section 257 is tapered relative to the rest of the tooth 252. In other versions of invention, the perimeter section 257 is stepped inwardly relative to the rest of the tooth 252.

Thus, it should be understood that a blade of this invention may be constructed so the perimeter of the lock tooth is flush with the perimeter of the adjacent section of the blade with which the tooth is associated. In still other versions of the invention, the blade is shaped so the perimeter of the lock tooth is located inwardly of the perimeter of the section of the blade with which the tooth is associated.

Alternative versions may be employed to form a blade of this invention out of single metal workpiece. For example, it is within the scope of this invention, that the whole of the blade, the lock tooth (or teeth) the blade body and the cutting teeth are formed out of material that is relatively soft. Then portions of the blade other than the lock teeth are selectively hardened.

One means of so manufacturing the blade is described by reference to the flow chart of FIG. 20. Initially, the blade or, more often plural blades, are cut from a relatively soft metal, step 280. One such metal is a 300 Series Stainless Steel such as a 316L Stainless Steel. This sheet has a thickness of approximately 0.4 mm. The blades are laser cut. In this cutting process, the basic perimeters of the cutting teeth and the blade body and formed. As part of this process, the lock teeth are partially shaped. More specifically the stock from which the blade is formed is shaped so as to define the outer perimeters of the lock teeth.

An optional part of step 280 is the machine grinding of the partially formed blade so as to sharpen the edges of the cutting teeth.

In a step 282 the whole of the blade is hardened. In one version of this method of the invention, the blade is hardened by diffusing a hardening agent into the blade. This agent is diffused into the blade below the surface of the blade. One hardening agent that can be diffused into the blade is carbon. For example, in one diffusion process, the blade is heated to a temperature between 400 and 600° C. Carbon is diffused into the whole of the blade to a depth of between 10 and 50 µm. One such process is the process of Kolsterising that is performed Bodycote plc of Macclesfield, Cheshire, United Kingdom. As a result of this diffusion of material into the blade, the blade has a hardened outer layer. This hardened outer layer extends to and is part of the lock teeth.

Figure 21:
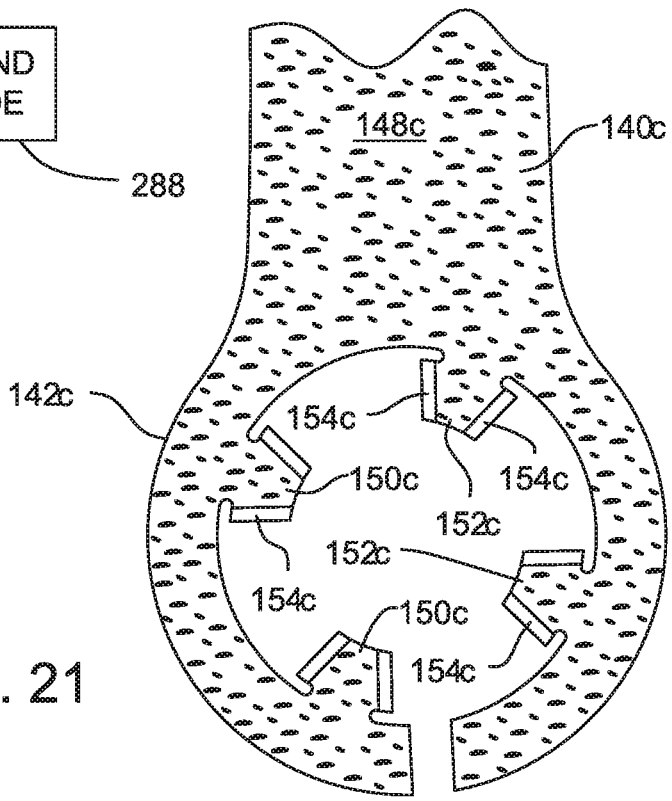
FIG. 21 is a plan view of the proximal end of a blade formed according to the method of FIG. 20.

Once the blade is hardened, in a step 284, sections of the hardened layer that are parts of the lock teeth are removed. For example, when the blade of FIG. 21 is fabricated, material is removed to define the wings 154b. The blade 140b of FIG. 21 is understood to be a variation of blade 140 of FIG. 11. The removal of this material removes the sections of the hardened layer that would have been above the wings 154b. The removal of material in step 284 may be accomplished by electro-discharge machining or grinding.

It should be understood that in this method of manufacture the bodies 152b of the lock teeth 150b retain their hardened outer layers. In FIG. 21, the hardened outer layer is represented by the stippling that extends of the blade body 148b as well as the bodies 152b of the lock teeth 150b. The absence of the stippling of the wings 154a of the lock teeth 150b represents that these sections of the lock teeth do not include the hardened outer layers. Thus, in these versions of the invention, while sections of the lock teeth 150b are relatively ductile, other sections of the lock teeth may be as hard the cutting teeth.

Once the blade is fully shaped, the blade is cleaned, sterilized and packaged, step 288. Upon the complete of step 288, the blade is ready for shipment and eventual use.

Figure 20:
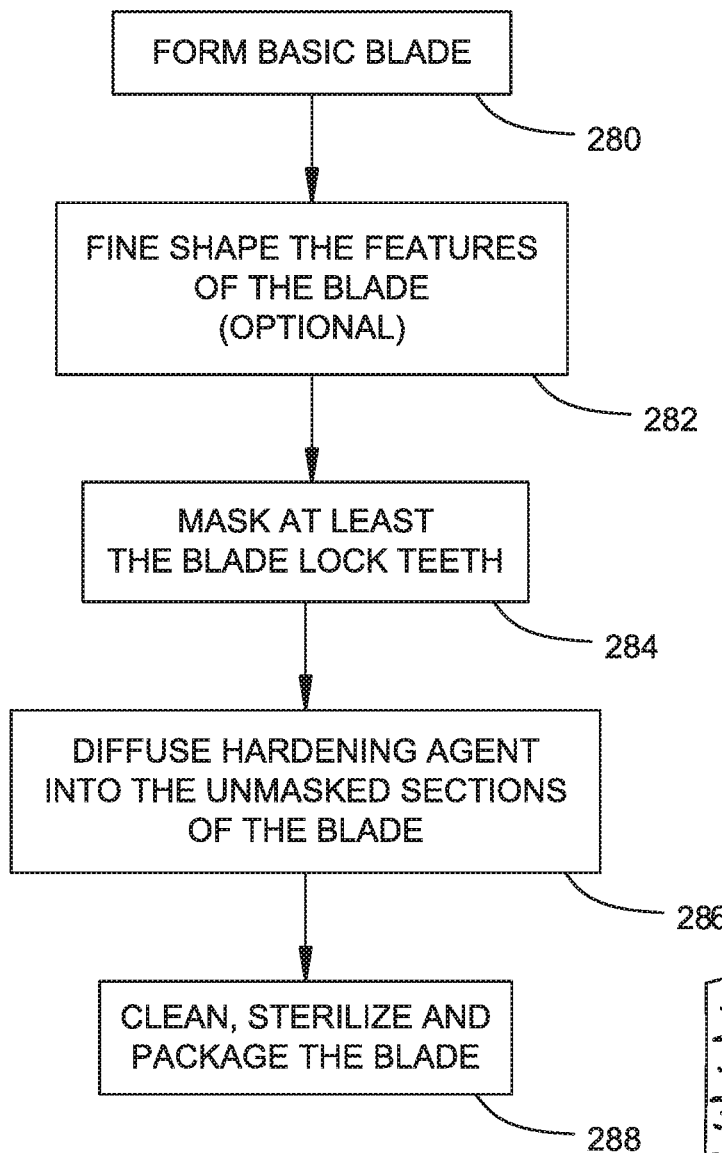
FIG. 20 is a flow chart of the process steps that are executed to fabricate a blade of this invention.

It should be understood that the method of FIG. 20 may be used to fabricate of a blade of this invention wherein the lock teeth have a constant thickness. In order to manufacture this version of the blade, a version of step 284 is executed so as to remove the hardened layers over the whole of each lock tooth.

In variations of the method of manufacture of FIG. 20, the hardened layer may be removed by laser etching, grinding or the selective application of an abrasive material against the lock teeth.

In a variation of this method of manufacture, the whole of the blade is formed. A mask is deposited over the sections of the lock teeth that are to remain relatively ductile. Once the mask is formed, the hardening agent is diffused into the blade. The sections of the blade into which the hardening agent is diffused thus develop a hardened outer layer. The mask prevents the hardening agent from diffusing into the mask section (or sections) of the lock teeth. After the mask is removed, these sections of the lock teeth are thus more ductile than at least the cutting teeth of the blade.

In some versions of this method of manufacture of this invention, the removal of the portions of the lock teeth to form the wings or other reduced thickness sections of the lock teeth is performed before the hardening agent is diffused in the blade so as to form the hardened outer layer. In other versions of this method of manufacture, after the hardening process is completed, the blade is subjected to the final shaping to form the reduced thickness sections of the lock teeth.

Other processes may be employed to harden at least the cutting teeth of the blade while leaving the lock teeth relatively soft and ductile. In an alternative process, the sections of the blade to be hardened are hardened by bombarding these sections of the blade with nitrogen ions. Alternatively, once the blade is formed a coating may be applied to at least the cutting teeth to harden these teeth relative to the lock teeth. One coating that can be applied is titanium nitride coating. An alternatively hardening coating that can be applied is a diamond like carbon coating.

In a variation of this process, the hardened coating is applied to the whole of the blade. The coating is then removed from the sections of the lock teeth that should be more ductile than the cutting teeth. The same process, electro-discharge machining, laser etching, grinding or abrasive application used to remove the hardened diffused layer may be employed to selectively remove the hardened coating.

Alternatively, when a coating is applied to harden at least the cutting teeth of the blade, a mask is applied to the sections of the blade that is not be provided with the coating. Once the coating process is completed, the mask is removed.

Another means to selectively harden at least the cutting teeth of the blade so they are harder than the lock tooth (or teeth) is a selective heating process. In a selectively hardening process, a laser is typically applied to the blade to only heat the portions of the blade to be hardened. The photonic energy of the laser is used to heat the portions of the blade to be hardened to a temperature that is higher than the annealing temperature of the material. The heated portion (or portions) of the blade are cooled. This cooling is performed at a rate that is typically faster than the rate of cooling for an annealing process. As a result of this rapid cooling, the heated portion (or portions) of the blade is (are) locked into a state in which it (they) are harder than prior to the heating.

From the above it should be clear that in some versions of the invention, the blade is fabricated so that the lock tooth (or teeth) and body are of the same hardness and only the cutting teeth is harder than the lock tooth (or teeth). Likewise, in some versions of the invention, the blade may be formed so sections of the blade body close to the cutting teeth are relatively hard and sections the blade body close to the lock tooth (or teeth) are softer.

For the purposes of this invention it is understood that a rasp is considered a species of a saw blade. A rasp is a file like cutting attachment. A rasp is typically, but not always, reciprocated back and forth along a line collinear with the longitudinal axis of the body of the rasp. A rasp 202a is generally seen in FIG. 18A. The rasp 202a is an alternative version of the reciprocating saw blade 202 of FIG. 18. The rasp 202a is formed so the teeth 242 extend outwardly from the major surfaces of the body 204. This is different from a conventional saw wherein the teeth project out from the edge surfaces of the blade body. When this invention is implemented as a rasp, the deformable lock tooth or lock teeth 210, 214, 218 extend outwardly from the body of the rasp in the vicinity of the proximal end of the body. The cutting teeth project outwardly from the major surfaces body of the rasp at the distal end of the rasp.

It should likewise be appreciated that the shapes of the saw unit anvil and press track the arrangement of lock held in place by the anvil and press. If the lock teeth are arranged linearly, than so are the features of the anvil and press that coin the lock teeth.

Also, while the invention is described as primarily for use as surgical saw, use of invention is not so restricted. The saw of this invention can have other applications. For example, the saw assembly of this invention can be used to cut material other than living tissue. This material includes and is not limited to wood, metal and plastic.

It is therefore an object of the appended claims to cover all such variations and modifications that come within the true spirit and scope of this invention.

The invention claimed is:
1. A surgical saw, the saw comprising:
a body;

a coupling assembly mounted to the body and adapted to releasably hold a saw blade to the coupling assembly, the coupling assembly including:
an anvil having one of a channel and a press foot,
a press having the other of the press foot and the channel wherein the press foot is capable of being received in the channel, and
a clamping assembly connecting the press and the anvil and selectively moving the press and the anvil towards and away from each other wherein, when the press is brought towards the anvil, the press foot presses a lock tooth of the saw blade into the channel so that the lock tooth is compressed between the anvil and the press to coin the lock tooth; and
a motor internal to the body connected to the anvil of the coupling assembly so as to reciprocate the coupling assembly and likewise reciprocate the saw blade held by the coupling assembly.

2. The surgical saw of claim 1, wherein:
the channel is defined by a space between two islands defined by one of the anvil and the press; and
a stop foot defined by the other of the anvil and the press, the stop foot being spaced from and adjacent to the press foot and the stop foot is positioned to seat against one of the islands when the press foot presses the lock tooth of the blade into the channel.

3. The surgical saw of claim 2, wherein a compress foot defined by the other of the anvil and the press, the compress foot being spaced from and adjacent to the press foot and is positioned to press against the blade when the press foot presses the lock tooth of the blade into the channel.

4. The surgical saw of claim 3, wherein the stop foot and the compress foot are defined by the other of the anvil and the press such that the stop foot and the compress foot extend the same distance from the other of the anvil and the press.

5. The surgical saw of claim 3, wherein a gap is defined between the press foot and the stop foot.

6. The surgical saw of claim 5, wherein at least a portion of the gap is positioned over the channel when the press foot presses the lock tooth of the blade into the channel.

7. The surgical saw of claim 1, wherein the press is a cap disposed over the anvil and the press foot extends outwardly from a surface of the cap.

8. The surgical saw of claim 1, wherein actuation of the motor reciprocates the anvil of the coupling assembly around an axis that extends through the anvil, the press, and the clamping assembly to reciprocate the saw blade around the axis.

9. The surgical saw of claim 1, wherein the clamping assembly comprises:
a threaded screw having a screw head and the screw head engaging the press; and
a pivot pin having a threaded bore and having a pin head engaging the anvil,
wherein the threaded screw is threaded into the threaded bore of the pivot pin and the screw passes through each of the anvil and the press and the pivot pin passes through the anvil, and
wherein selective rotation of the screw relative to the pin moves the press and the anvil toward and away from each other.

10. The surgical saw of claim 9, wherein the screw includes a compress foot and one of a knob and a pivotable arm is fixed to the compress foot for unitary rotation with the screw.

11. The surgical saw of claim 10, wherein the pivotable arm defines an arm longitudinal axis and is pivotably fixed to the compress foot and the pivotable arm has a locked position substantially parallel with a body longitudinal axis defined by the body.

12. The surgical saw of claim 10, wherein the pivotable arm defines an arm longitudinal axis and is pivotably fixed to the compress foot and the pivotable arm has a locked position where the arm longitudinal axis is substantially parallel with a body longitudinal axis defined by the body and extends in a proximal direction.

13. The surgical saw of claim 9, wherein the anvil further comprising a bearing assembly, the bearing assembly configured to rotatably support the pivot pin such that that pivot pin is rotatably engaged with the anvil.

14. The surgical saw of claim 13, wherein the bearing assembly comprises an inner race, an outer race, and ball bearing disposed between the inner race and the outer race to provide rotating interface between the inner race and the outer race.

15. The surgical saw of claim 14, wherein the pin head is disposed against a portion of the inner race of the bearing assembly of the anvil.

* * * * *